US008483351B2

(12) United States Patent
Wang et al.

(10) Patent No.: US 8,483,351 B2
(45) Date of Patent: Jul. 9, 2013

(54) CARDIAC COMPUTED TOMOGRAPHY METHODS AND SYSTEMS USING FAST EXACT/QUASI-EXACT FILTERED BACK PROJECTION ALGORITHMS

(75) Inventors: Ge Wang, Blacksburg, VA (US); Jun Zhao, Shanghai (CN); Yang Lu, Shanghai (CN); Hengyong Yu, Winston-Salem, NC (US); Alexander Katsevich, Oviedo, FL (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 12/914,790

(22) Filed: Oct. 28, 2010

(65) Prior Publication Data

US 2012/0039434 A1 Feb. 16, 2012

Related U.S. Application Data

(60) Provisional application No. 61/255,708, filed on Oct. 28, 2009.

(51) Int. Cl.
*A61B 6/00* (2006.01)

(52) U.S. Cl.
USPC .......................................................... 378/4

(58) Field of Classification Search
USPC .......................................................... 378/4
See application file for complete search history.

(56) References Cited

U.S. PATENT DOCUMENTS

| | | | |
|---|---|---|---|
| 4,651,002 A | 3/1987 | Anno | |
| 4,656,650 A | 4/1987 | Kikuchi | |
| 5,313,511 A | 5/1994 | Annis et al. | |
| 5,383,119 A * | 1/1995 | Tam | 378/8 |
| 5,604,778 A * | 2/1997 | Polacin et al. | 378/9 |
| 5,909,476 A | 6/1999 | Cheng | |
| 5,966,422 A * | 10/1999 | Dafni et al. | 378/9 |
| 5,987,095 A | 11/1999 | Chapman et al. | |
| 6,002,743 A | 12/1999 | Telymonde | |
| 6,175,609 B1 | 1/2001 | Edic | |
| 6,240,157 B1 * | 5/2001 | Danielsson | 378/15 |
| 6,333,960 B1 | 12/2001 | Tam | |
| 6,429,434 B1 | 8/2002 | Watson | |
| 6,463,118 B2 | 10/2002 | Besson | |
| 6,574,299 B1 * | 6/2003 | Katsevich | 378/15 |
| 6,804,321 B2 * | 10/2004 | Katsevich | 378/4 |
| 6,850,585 B2 | 2/2005 | Hsieh | |
| 6,934,353 B2 | 8/2005 | Wang | |
| 6,983,034 B2 | 1/2006 | Wang | |

(Continued)

OTHER PUBLICATIONS

Katsevich, Theoretically Exact Filtered Backprojection-Type Inversion Algorithm for Spiral CT, Siam J Appl Math, vol. 62, No. 6, 2002, pp. 2012-2026.*

(Continued)

*Primary Examiner* — Alexander H Taningco
(74) *Attorney, Agent, or Firm* — New River Valley IP Law; Michele L. Mayberry

(57) ABSTRACT

The present invention provides systems, methods, and devices for improved computed tomography (CT). More specifically, the present invention includes methods for improved cone-beam computed tomography (CBCT) resolution using improved filtered back projection (FBP) algorithms, which can be used for cardiac tomography and across other tomographic modalities. Embodiments provide methods, systems, and devices for reconstructing an image from projection data provided by a computed tomography scanner using the algorithms disclosed herein to generate an image with improved temporal resolution.

11 Claims, 23 Drawing Sheets

U.S. PATENT DOCUMENTS

| | | | | |
|---|---|---|---|---|
| 7,042,975 | B2* | 5/2006 | Heuscher | 378/8 |
| 7,058,440 | B2 | 6/2006 | Heuscher | |
| 7,085,343 | B2 | 8/2006 | Shinno | |
| 7,145,980 | B2 | 12/2006 | Sakaguchi | |
| 7,263,164 | B2 | 8/2007 | Ghelmansarai et al. | |
| 7,372,937 | B2 | 5/2008 | Wang | |
| 7,697,658 | B2 | 4/2010 | Wang | |
| 7,840,249 | B2 | 11/2010 | Wang | |
| 2002/0077543 | A1 | 6/2002 | Grzeszczuk | |
| 2003/0007593 | A1 | 1/2003 | Heuscher | |
| 2003/0076920 | A1 | 4/2003 | Shinno | |
| 2003/0161444 | A1* | 8/2003 | Katsevich | 378/210 |
| 2004/0125910 | A1* | 7/2004 | Katsevich | 378/15 |
| 2005/0152494 | A1* | 7/2005 | Katsevich | 378/62 |
| 2006/0029180 | A1* | 2/2006 | Katsevich | 378/4 |
| 2007/0036418 | A1* | 2/2007 | Pan et al. | 382/131 |
| 2008/0056432 | A1 | 3/2008 | Pack | |
| 2009/0196393 | A1 | 8/2009 | Wang | |
| 2010/0140485 | A1 | 6/2010 | Mishra | |
| 2010/0202583 | A1 | 8/2010 | Wang | |
| 2010/0310037 | A1 | 12/2010 | Wang | |

OTHER PUBLICATIONS

Katsevich, Theoretically Exact Filtered BAckprojection-type Inversion Algorithm for Spiral CT, Siam J. Appl, Math, vol. 62, No. 6, 2002, pp. 2012-2026.*

Kudo et al., Exact and approximate algorithms for helical cone-beam CT, Phys Med Biol, 49, 2004, pp. 2913-2931.*

Achenbach, S., et al., Contrast-enhanced coronary artery visualization by dual-source computed tomography—Initial experience. European Journal of Radiology, 2006. 57(3): p. 331-335.

Beck, A. and M. Teboulle (2009). "A Fast Iterative Shrinkage-Thresholding Algorithm for Linear Inverse Problems." Siam Journal on Imaging Sciences 2(1): 183-202.

Bharkhada, D., et al., Cardiac CT radiation dose reduction using interior reconstruction algorithm with the aorta and vertebra as known information. Journal of Computer Assisted Tomography, 2007. To appear.

Bharkhada, D., et al., Line-source based x-ray tomography. International journal of biomedical imaging, 2009. 2009 (Article ID 534516): p. 8.

Boas, D. et al., "Imaging the body with diffuse optical tomography," IEEE Signal Processing Magazine, vol. 18, pp. 57-75, 2001.

Candes, E. and J. Romberg, Robust signal recovery from incomplete observations. 2006 IEEE International Conference on Image Processing, ICIP 2006, Proceedings, 2006: p. 1281-1284.

Candes, E. and J. Romberg. Signal Recovery from Random Projections. in Computational Imaging III, Proceedings of SPIE vol. 5764. 2005.

Candes, E.J., J.K. Romberg, and T. Tao, Stable signal recovery from incomplete and inaccurate measurements. Communications on Pure and Applied Mathematics, 2006. 59(8): p. 1207-1223.

Candes, E.J.; J. Romberg, and T. Tao, Robust uncertainty principles: Exact signal reconstruction from highly incomplete frequency information. IEEE Transactions on Information Theory, 2006. 52(2): p. 489-509.

Cao, G., et al. A dynamic micro-CT scanner with a stationary mouse bed using a compact carbon nanotube field emission x-ray tube. In SPIE-Med. Imaging 2009. 2009.

Cao, G., et al., A dynamic micro-CT scanner based on a carbon nanotube field emission x-ray source. Physics in Medicine and Biology, 2009. 54 p. 2323-2340.

Cao, G.H., et al. Respiratory-gated micro-CT using a carbon nanotube based micro-focus field emission x-ray source—art. No. 691304. in Medical Imaging 2008 Conference. 2008. San Diego, CA: Spie-Int Soc Optical Engineering.

Castro, C.R.F., et al., Coherent scattering characteristics of normal and pathological breast human tissues. Radiation Physics and Chemistry, 2004. 71(3-4): p. 649-651.

Chapman, D., et al., Diffraction enhanced x-ray imaging. Physics in Medicine and Biology, 1997. 42(11): p. 2015-2025.

Chen, Guang-Hong, et al., Small-angle scattering computed tomography (SAS-CT) using a Talgot-Lau interferometer and a rotating anode x-ray tube: theory and experiments, Optics Express, vol. 18, No. 12, pp. 12960-12970, Jun. 7, 2010.

David, C., et al., Fabrication of diffraction gratings for hard X-ray phase contrast imaging. Microelectronic Engineering, 2007. 84(5-8): p. 1172-1177.

Defrise M et al. Truncated Hilbert transform and image reconstruction from limited tomographic data. Inverse Problems 2006; 22(3):1037-1053.

Denis, E., et al., Automatic quality control of digitally reconstructed radiograph computation and comparison with standard methods. Medical Imaging 2007: Physics of Medical Imaging, edited by Jiang Hsieh, Michael J. Flynn, Proc. of SPIE vol. 6510, 65104J.

Fernandez, M., et al., Small-angle x-ray scattering studies of human breast tissue samples. Physics in Medicine and Biology, 2002. 47(4): p. 577-592.

Flohr, T.G.; C. H. McCollough, H. Bruder, M. Petersilka, K. Gruber, C. Süß, M. Grasruck, K. Stierstorfer, B. Krauss, and R. Raupach, "First performance evaluation of a dual-source CT (DSCT) system," European Radiology, vol. 16, pp. 256-268, 2006.

Guang Yang, et al. Stationary digital breast tomosynthesis system with a multi-beam field emission x-ray source array in SPIE proceeding on Medical Imaging. 2008.

Hamaker, C. et al., The Divergent beam X-ray transform. Rocky Mountain Journal of Mathematics, 1980. 10(1): p. 253-283.

Johnson, T.R.C., et al., Dual-source CT cardiac imaging: initial experience. European Radiology, 2006. 16(7): p. 1409-1415.

Jung, H., et al., k-t FOCUSS: A general compressed sensing framework for high resolution dynamic MRI. Magnetic Resonance in Medicine, 2008: p. to appear.

Kak, A.C. and M. Slaney, Principles of Computerized Tomographic Imaging. 2001: Society of Industrial and Applied Mathematics.

Kapralov, M.; and A. Katsevich, "A one-PI algorithm for helical trajectories that violate the convexity condition," Inverse Problems, vol. 22, pp. 2123-2143, 2006.

Kapralov, M.; and A. Katsevich. "On the study of 1PI algorithms for a general class of curves". SIAM Journal on Imaging Sciences. vol. 1, pp. 418-459, 2008.

Katsevich, A., "3PI algorithms for helical computer tomography," Advances in Applied Mathematics, vol. 36, pp. 213-250, 2006.

Katsevich, A., "A General Scheme for Constructing Inversion Algorithms for Cone Beam CT", Hindawi Publishing Corp, Sep. 30, 2002, pp. 1-17.

Katsevich, A., "Singular value decomposition for the truncated Hilbert transform", Inverse Problems 26, Sep. 30, 2010, pp. 1-12.

Katsevich, A., "Singular value decomposition for the truncated Hilbert transform: Part II", Inverse Problems 27, Jun. 8, 2011, pp. 1-7.

Katsevich, A., "Theoretically exact filtered backprojection-type inversion algorithm for spiral CT," SIAM Journal on Applied Mathematics, vol. 62, No. 6, pp. 2012-2026, 2002.

Kottler, C., et al., Grating interferometer based scanning setup for hard x-ray phase contrast imaging. Review of Scientific Instruments, 2007. 78(4): p. 43710.

Kudo, H.; M. Courdurier, F. Noo, and M. Defrise, "Tiny a priori knowledge solves the interior problem in computed tomography," Phys. Med. Biol, vol. 53, pp. 2207-2231, 2008.

Kyriakou Y.; and W. Kalender, "Efficiency of antiscatter grids for flat-detector CT," Physics in Medicine and Biology, vol. 52, pp. 6275-6293, 2007.

LaRoque, S.J., E.Y. Sidky, and X. Pan, Accurate image reconstruction from few-view and limited-angle data in diffraction tomography. Journal of the Optical Society of America A-Optics Image Science and Vision, 2008. 25(7): p. 1772-1782.

Lu, Yang, et al., "Fast Exact/Quasi-Exact FBP Algorithms for Triple-Source Helical Cone-Beam CT," IEEE Transactions on Medical Imaging, vol. 29, No. 3, Mar. 2010.

Matsumoto, M., et al., Fabrication of diffraction grating for X-ray Talbot interferometer. Microsystem TechnologiesMicro-and Micro- and Nanosystems-Information Storage and Processing Systems, 2007. 13(5-6): p. 543-546.

Momose, A., et al., Biomedical imaging by Talbot-type X-ray phase tomography, in Developments in X-Ray Tomography V, U. Bonse, Editor. 2006, SPIE-Int Society Optical Engineering: Bellingham. p. T3180.

Momose, a., et al., Phase-contrast X-ray computed tomography for observing biological soft tissues (vol. 2, p. 473, 1996). Nature Medicine, 1996. 2(5): p. 596-596.

Momose, A., Recent advances in X-ray phase imaging. Japanese Journal of Applied Physics Part 1-Reg. Papers Brief Comm. & Rev. Papers, 2005. 44(9A): p. 6355-6367.

Noo, F.; J. Pack, D. Heuscher., "Exact helical reconstruction using native cone-beam geometries," Physics in Medicine and Biology, vol. 48, pp. 3787-3818, 2003.

Orlov, S.S., "Theory of three-dimensional reconstruction. 1. Conditions of a complete set of projections," Soy. Phys. Crystallogr, vol. 20, pp. 312-314, 1975.

Pfeiffer, F., et al., Hard-X-ray dark-field imaging using a grating interferometer. Nature Materials, 2008. 7(2): p. 134-137.

Pfeiffer, F., et al., High-resolution brain tumor visualization using three-dimensional x-ray phase contrast tomography. Phy. in Med. and Bio. 2007. 52(23):p. 6923-6930.

Pfeiffer, E, et al., Phase retrieval and differential phase-contrast imaging with low-brilliance X-ray sources. Nature Physics, 2006. 2(4): p. 258-261.

Poludniowski, G. et al., "An efficient Monte Carlo-based algorithm for scatter correction in keV cone-beam CT," Phys. in Medicine and Biology, vol. 54, pp. 3847-3864, 2009.

Rudin, L. I., S. Osher, et al. (1992). "Nonlinear Total Variation Based Noise Removal Algorithms." Physica D 60(1-4): 259-268.

Sidky, E.Y. C.M. Kao, and X.H. Pan, Accurate image reconstruction from few-views and limited-angle data in divergent-beam CT. Journal of X-Ray Science and Technology, 2006. 14(2): p. 119-139.

Siewerdsen, J. et al., "A simple, direct method for x-ray scatter estimation and correction in digital radiography and cone-beam CT," Medical Physics, vol. 33, p. 187, 2006.

Sprenger, F., et al., Distributed source x-ray tube technology for tomosynthesis imaging. Medical Imaging 2010: Physics of Medical Imaging, edited by Ehsan Samei, Norbert J. Pelc, Proc. Of Spie vol. 7622, 76225M.

Strobl, M. and Treimer, W., "Small angle scattering signals for (neutron) computerized tomography," Applied Physics Letters, vol. 85, No. 3, pp. 488-490, Jul. 19, 2004.

Vannier, M.; and G. Wang, "Spiral CT refines imaging of temporal bone disorders," Diagnostic imaging, vol. 15, p. 116-121, 1993.

Vogel, C.R. and M.E. Oman, Fast, robust total variation-based reconstruction of noisy, blurred images. Ieee Transactions on Image Processing, 1998. 7(6): p. 813-824.

Wang Ge ; Yu Hengyong. Can interior tomography outperform lambda tomography? PNAS (Jun. 1, 2010), vol. 107, Issue 22, pp. E92-E93.

Wang, G. and M. Jiang, Ordered-Subset Simultaneous Algebraic Reconstruction Techniques (OS-SART). J. of X-ray Science and Tech., 2004. 12(3): p. 169-177.

Wang, G., et al., Half-scan cone-beam x-ray microtomography formula. Journal of Scanning Microscopy 1994. 16(4): p. 216-220.

Wang, G., et al., Top-level design and preliminary physical analysis for the first electron-beam micro-CT scanner. Journal of X-Ray Sci. and Tech., 2004. 12(4): p. 251-260.

Wang, G., G. Schweiger, and M.W. Vannier, An iterative algorithm for X-ray CT fluoroscopy. IEEE Trans Med Imaging, 1998. 17(5): p. 853-856.

Wang, G., H. Yu, and B. De Man, An Outlook on X-ray CT Research and Development (invited paper). Medical Physics, 2008. 35(3): p. 1051-1064.

Wang, G., H. Yu, and Y. Ye, A scheme for multisource interior tomography. Med. Phys., 2009. 36(8): p. 3575-3581.

Wang, G.; C. R. Crawford, and W. A. Kalender, "Guest editorial-Multirow detector and cone-beam spiral/helical CT," Medical Imaging,IEEE Transactions on, vol. 19, pp. 817-821, 2000.

Wang, G. S. Zhao, H. Yu, C. Miller, P. Abbas, B. Gantz, S. Lee, and J. Rubinstein, "Design, analysis and G.; simulation for development of the first clinical micro-CT scanner1," Academic Radiology, vol. 12, pp. 511-525, 2005.

Wang, G.; T.-H. Lin, P.-C. Cheng, and D. M. Shinozaki, "A general cone-beam reconstruction algorithm," IEEE Transactions on Medical Imaging, vol. 12, p. 486, 1993.

Wang, G.; Y. Ye, and H. Yu, "Approximate and exact cone-beam reconstruction with standard and non-standard spiral scanning," Physics in Medicine and Biology, vol. 52, pp. 1-13, 2007.

Wang, Ge et al., Varying Collimation for Dark-Field Extraction, Accepted Nov. 12, 2009, pp. 1-7, vol. 2009, International Journal of Biomedical Imaging, vol. 2009, Hindawi Publishing Corporation.

Ye et al., A General Local Reconstruction approach Based on a Truncated Hilbert Transform, Jun. 18, 2007, International Journal of Biomedical Imaging, Article ID 63634, 8 pages.

Ye YB, Yu HY, Wang G. Exact interior reconstruction with cone-beam CT. International Journal of Biomedical Imaging 2007; 2007:5. Article ID: 10693.

Ye, Y.B. and G. Wang, Filtered backprojection formula for exact image reconstruction from cone-beam data along a general scanning curve. Medical Physics, 2005. 32(1): p. 42-48.

Yu Hy, Wang G. Studies on implementation of the Katsevich algorithm for spiral cone-beam CT. Journal of X-ray Science and Technology 2004; 12(2):96-117.

Yu, H. and G. Wang, Compressed sensing based interior tomography. Physics in Medicine and Biology 2009. 54: p. 2791-2806.

Yu, H.Y., Y. C. Wei, et al. (2007). "Lambda tomography with discontinuous scanning trajectories." Physics in Medicine and Biology 52(14): 4331-4344.

Yu, H., et al. Compressive sampling based interior reconstruction for dynamic carbon nanotube micro-CT, Journal of X-ray Science and Technology, 17(4):295-303, 2009.

Yu, H., et al., Ultra-Low Dose Lung CT Perfusion Regularized by a Previous Scan. Academic Radiology, 2009. 16(3): p. 363-373.

Yu, H. J. Yang, et al. (2009). "Supplemental analysis on compressed sensing based interior tomography." Phys Med Biol 54(18): N425-N432.

Yu, H., Y. Ye, and G. Wang, Interior reconstruction using the truncated Hilbert transform via singular value decomposition. Journal of X-Ray Science and Technology, 2008. 16(4): p. 243-251.

Yu, H.Y.; J.S. Yang, M. Jiang and G. Wang, Interior SPECT-exact and stable ROI reconstruction from uniformly attenuated local projections. Communications in Numerical Methods in Engineering, 2009. 25(6): p. 693-710.

Zeng, K., et al., Digital tomosynthesis aided by low-resolution exact CT. Journal of Computer Assisted Tomography, 2007. 31(6): p. 976-983.

Zhao, J.; M. Jiang, T. Zhuang, and G. Wang, "An exact reconstruction algorithm for triple-source helical cone-beam CT," Journal of X-Ray Science and Technology, vol. 14, p. 191, 2006.

Zhao, J.; M. Jiang, T. Zhuang and G. Wang, "Minimum detection window and inter-helix PI-line with triple-source helical cone-beam scanning", Journal of X-Ray Science and Technology, 14:95-107, 2006.

Zhao, J.; Y. Jin, Y. Lu and G. Wang, "A Filtered Backprojection Algorithm for Triple-Source Helical Cone-Beam CT," Medical Imaging, IEEE Transactions on, vol. 28, pp. 384-393, 2009.

Zitova, et al., Image Registration Methods: A Survey; 24 pgs., Image and Vision Computing 21 (2003) 977-1000.

* cited by examiner

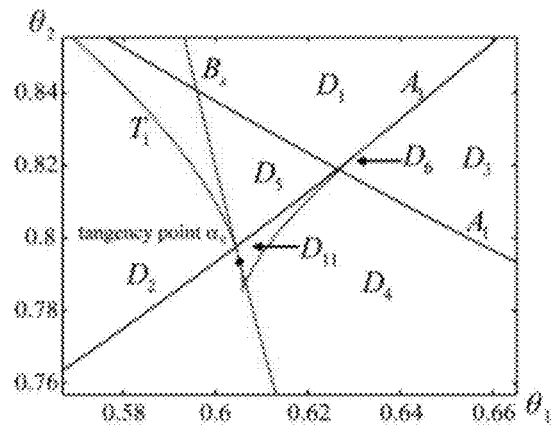
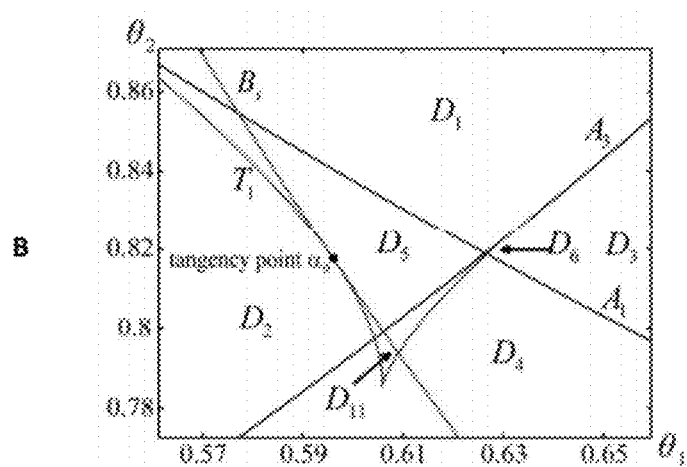
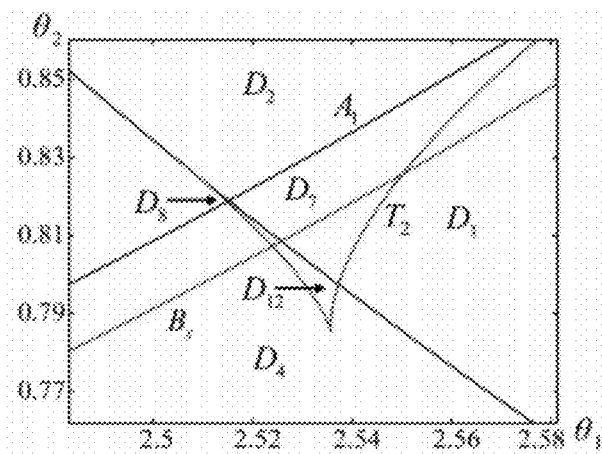
FIGS. 11A-C

A
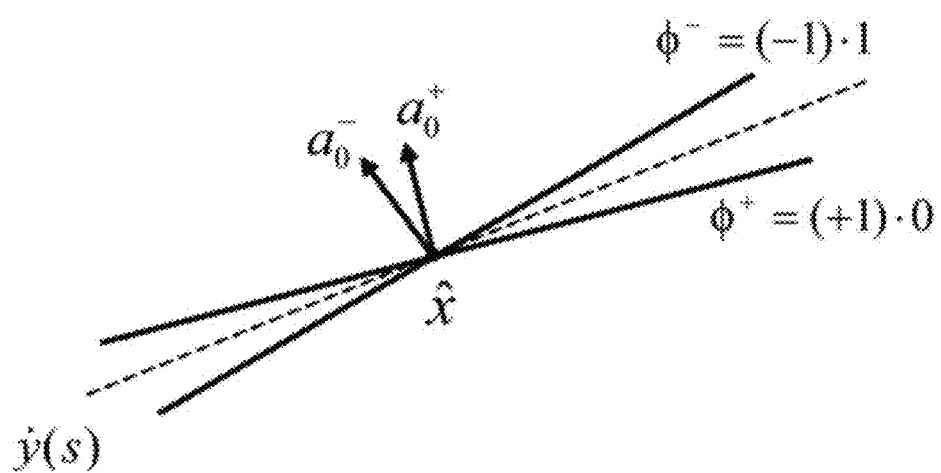
B
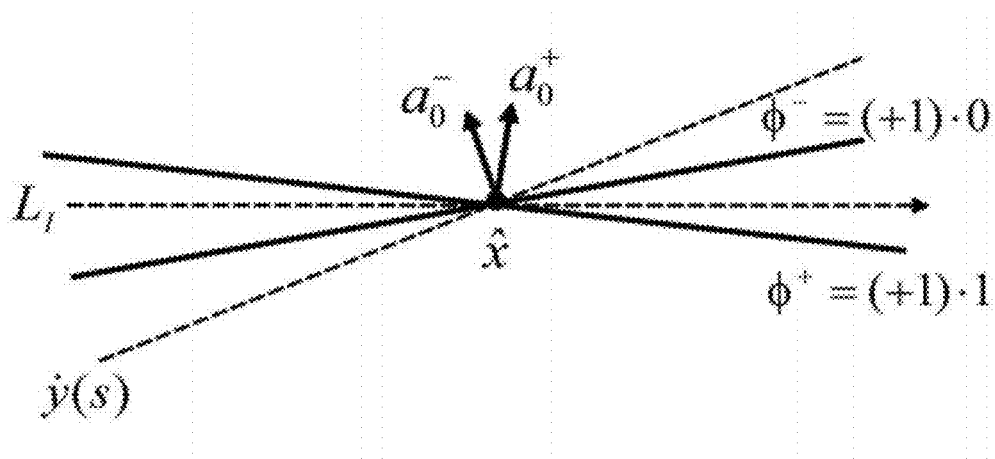
FIGS. 12A-B

A
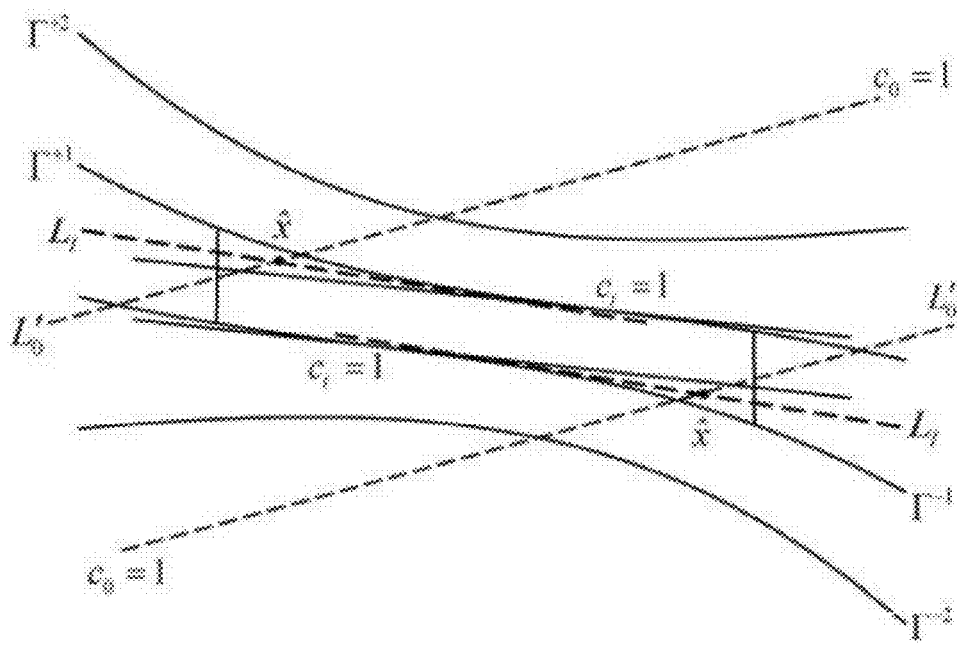
B
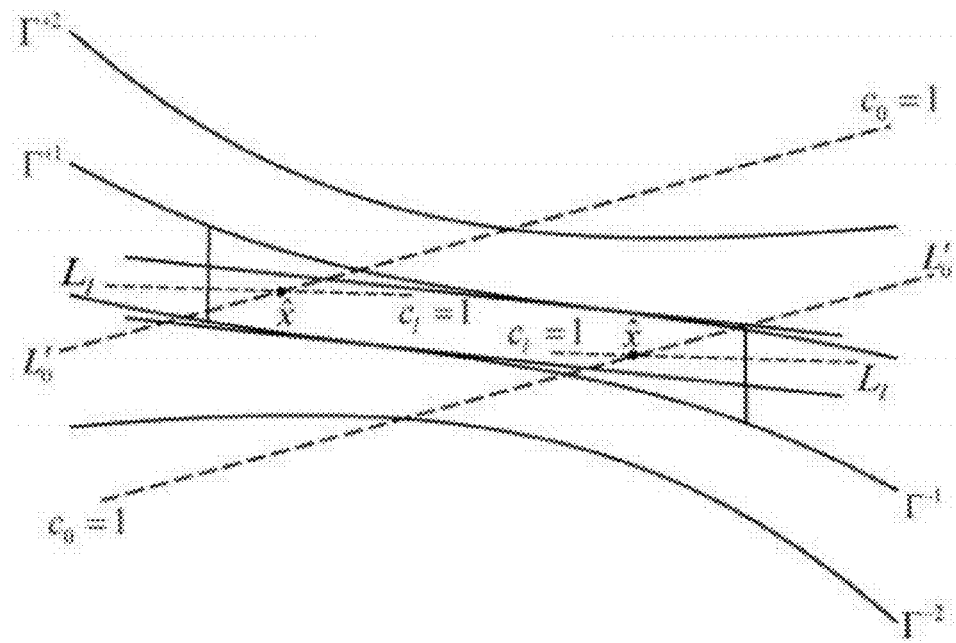
FIGS. 13A-B

CARDIAC COMPUTED TOMOGRAPHY METHODS AND SYSTEMS USING FAST EXACT/QUASI-EXACT FILTERED BACK PROJECTION ALGORITHMS

CROSS-REFERENCE TO RELATED APPLICATIONS

This application claims priority to and the benefit of the filing date of U.S. Provisional Application No. 61/225,708, filed Oct. 28, 2009, which is incorporated by reference herein in its entirety.

STATEMENT OF GOVERNMENT INTEREST

This invention was made made with government support under contracts EB002667, EB004287 and EB007288 awarded by National Institutes of Health. The government has certain rights in the invention.

BACKGROUND OF THE INVENTION

1. Field of the Invention

The present invention provides systems, methods, and devices for improved computed tomography (CT). More specifically, the present invention includes methods for improved cone-beam computed tomography (CBCT) resolution using improved filtered back projection (FBP) algorithms, which can be used for cardiac tomography and across other tomographic modalities.

2. Description of Related Art

Cardiovascular diseases (CVDs) are pervasive (American Heart Association 2004). CVD is the number one killer in the western world. The cost of the health care for CVD is skyrocketing. In 2004, the estimated direct and indirect cost of CVD was $368.4 billion.

Coronary artery disease is a leading cause of death as a result of a myocardial infarct (heart attack) without any symptom. Tomographic equipment with high temporal resolution is needed in order to successfully perform a cardiac scan and understand the etiology and pathogenesis of CVD, such as high blood pressure, coronary artery diseases, congestive heart failure, stroke and congenital cardiovascular defects, as well as to develop effective prevention and treatment strategies. CT scanners are now considered instrumental for detecting early heart diseases and are a centerpiece of preventive cardiology programs.

Although there has been an explosive growth in the development of CT scanners for cardiac CT studies, the efforts are generally limited to regular heartbeats. When applying traditional CT algorithms for cardiac CT reconstruction, the cardiac images may be inaccurate or useless based on substantial motion blurring, especially seen in patients who have high and irregular heartbeats due to the fact that each projection sector covers a projection angular range of a substantial length. Within such an angular range, the heart moves appreciably, especially when it is not in a relative stationary phase. As a benchmark, a ~0.3 mm spatial resolution is routinely achieved in spiral CT of the temporal bone where the motion magnitude is much less than that of the heart (see M. Vannier and G. Wang, Spiral C T refines imaging of temporal bone disorders, *Diagnostic imaging*, vol. 15, p. 116-121, 1993 and G. Wang, et al., Design, analysis and simulation for development of the first clinical micro-CT scanner1, *Academic Radiology*, vol. 12, pp. 511-525, 2005, which is incorporated by reference herein in its entirety). Spatial resolution with cardiac CT is at best in the millimeter domain.

Over the last thirty years, computer tomography (CT) has gone from image reconstruction based on scanning in a slice-by-slice process to spiral scanning. From the mid-1980s to present day, spiral type scanning has become the preferred process for data collection in CT. Under spiral scanning, a table with the patient continuously moves through the gantry while the source in the gantry is continuously rotating about the table. At first, spiral scanning used a one-dimensional detector array, which received data in one dimension (a single row of detectors). Later, two-dimensional detectors, where multiple rows (two or more rows) of detectors sit next to one another, were introduced. In CT there have been significant problems for image reconstruction especially for two-dimensional detectors.

For three/four-dimensional (also known as volumetric/dynamic) image reconstruction from the data provided by a spiral scan with two-dimensional detectors, known groups of algorithms include: exact algorithms, quasi-exact algorithms, approximate algorithms, and iterative algorithms. While the best approximate algorithms are of Feldkamp-type, the state of the art of the exact algorithms is the recently developed Katsevich algorithm.

Under ideal circumstances, exact algorithms can provide a replication of a true object from data acquired from a spiral scan. However, exact algorithms can require a larger detector array, more memory, are more sensitive to noise, and run slower than approximate algorithms. Approximate algorithms can produce an image very efficiently using less computing power than exact algorithms. However, even under typical circumstances they produce an approximate image that may be similar to but still different from the exact image. In particular, approximate algorithms can create artifacts, which are false features, in an image. Under certain circumstances these artifacts can be quite severe.

To perform the long object reconstruction with longitudinally truncated data, the spiral cone-beam scanning mode and a generalized Feldkamp-type algorithm were proposed by Wang and others in 1991. However, the earlier image reconstruction algorithms for that purpose are either approximate or exact only using data from multiple spiral turns.

In 2002, an exact and efficient method was developed by Katsevich, which is a significant breakthrough in the area of spiral cone-beam CT. The Katsevich algorithm is in a filtered-backprojection (FBP) format using data from a PI-arc (scanning arc corresponding to the PI-line and less than one turn) based on the so-called PI-line and the Tam-Danielsson window. The principle is that any point inside the standard spiral or helical belongs to one and only one PI-line. Any point on the PI-line can be reconstructed from filtered data on the detector plane with the angular parameter from the PI-arc. In 2003, a slow FBP and a backprojected-filtration algorithm (BPF) were developed for helical cone-beam CT based on the Katsevich algorithm by exchanging the order of integrals. For important biomedical applications including application with movement present such as cardiac CT, generalization of the exact cone-beam reconstruction algorithms from the case of standard spirals to the case of nonstandard spirals and other scanning loci is desirable and useful. Although the current Katsevich-type algorithms are known for a standard spiral scan, there are no known fast algorithms, systems, devices and methods that can reconstruct an image exactly or quasi-exactly from data acquired in a CT scan with good temporal resolution.

Therefore, despite the impressive advancement of the CT technology, there are still unmet, critical and immediate needs such as those mentioned above for better image quality in many cardiac and other CT investigations wherein the motion magnitude is increased.

SUMMARY OF THE INVENTION

The numerous limitations inherent in the scanning systems described above provide great incentive for new, better systems and methods capable of accounting for one or more of these issues. If CTs are to be seen as an accurate, reliable therapeutic answer, then improved methods for reconstructing an image should be developed that can more accurately predict the image with improved temporal resolution and less artifacts.

The primary limitation to the above-mentioned system is its need to provide good temporal resolution and image reconstruction when movement is involved. However, as more complex applications for scanning are encountered, reconstruction of key subject areas such as the heart, lung, head and neck is cumbersome at best and may be inadequate to develop reliable diagnosis and therapies. Therefore, a more-advanced system that allows for the production of better object reconstruction would be ideal. This allows for the adaptation of exact and quasi-exact algorithms to provide better images.

Accordingly, embodiments of the invention provide methods, systems, and devices for reconstructing an image from projection data provided by a computed tomography scanner comprising: scanning an object in a cone-beam imaging geometry following a general triple helix path wherein projection data is generated; reconstructing the image, wherein the reconstructing comprises performing a filtered backprojection; using a fast exact or quasi-exact filtered back projection algorithm to generate the backprojected data; and using the backprojected data to generate an image with improved temporal resolution. Preferably, embodiments of the invention provide images with less than about 500 ms, e.g., about 100 ms temporal resolution or less, such as about 80 ms or less, or about 60 ms or less, or about 50 ms or less, or about 30 ms or less, or even about 10 ms or less, and so forth.

In the context of this disclosure, exact or quasi-exact means that the algorithm is theoretically exact for a good portion of voxels in the object or theoretically exact if a practically insignificant portion of data could be handled in a more complicated fashion. Said another way, quasi-exact means that the algorithm is derived from an exact three-dimensional reconstruction approach, in which deviations from exactness are introduced which are sufficiently small and lead to minor artifacts, but result in a numerically efficient algorithm. By way of example, these deviations may lead to inexact weighting of a small percentage of Radon planes at every voxel.

In preferred embodiments, the temporal resolution may be in the range of about 100 ms to less than about 10 ms.

The present invention includes a computed tomography (CT) imaging method comprising: scanning an object using multi-source helical cone-beam computed tomography (CBCT) to acquire projection data relating to the object; and reconstructing the scanned portion of the object into an image by performing a computationally efficient filtered backprojection (FBP) and theoretically exact/quasi-exact algorithm to generate image data. Such methods, for example, are included within the scope of the invention which are capable of achieving a temporal resolution in the image in the range of <500 ms.

In the context of this disclosure, what is meant by "computationally efficient", we mean that the computational efficiency of a cone-beam reconstruction algorithm is in the same order of magnitude of that developed by Katsevich as reported in (A. Katsevich, "Theoretically exact filtered backprojection-type inversion algorithm for spiral CT," SIAM Journal on Applied Mathematics, vol. 62, p. 2012, 2002), which is herein incorporated by reference in its entirety. Further, by "theoretically exact", we mean that the reconstructed image would be exact if both the sampling interval and the measurement error approach zero.

Embodiments of the invention further include a computed tomography (CT) imaging system comprising: a multi-source helical cone-beam computed tomography (CBCT) scanner operably configured for scanning an object to acquire projection data relating to the object; a processing module operably configured for reconstructing the scanned portion of the object into an image by performing a filtered backprojection (FBP) with a fast exact or quasi-exact FBP algorithm to generate image data; and a processor for executing the processing module. Such systems can include software and hardware operably configured for performing the functions of the processing module.

Embodiments of the present invention provide for reconstructing the image using a fast exact or quasi-exact algorithm developed by defining the weight function, determining filtering directions, calculating the backprojection coefficients, and reconstructing the object with, for example:

$$f(x) = -\frac{1}{4\pi^2} \int_I \sum_m \frac{c_m(s,x)}{|x-y(s)|} \times \int_0^{2\pi} \frac{\partial}{\partial q} D_f(y(q), \cos\gamma\beta(s,x) + \sin\gamma\alpha^\perp(s,x,\theta_m))\bigg|_{q=s} \frac{dy}{\sin\gamma} ds.$$

Such methods, systems, and devices can further be characterized in having the fast exact or quasi-exact algorithm implemented by differentiating each projection with respect to variable s; for each $y_i(s)$, $i=\{1, 2, 3\}$, performing the Hilbert transform of derivative data along the given filtering directions on the corresponding detector plane; and backprojecting the filtered data on the inter-PI segments to reconstruct the object.

The features and advantages of the present invention will be apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 11A is a graphical representation of the $B_s$-curve being tangent to a T-curve in $D_{11}$ for the source on $y_1(s)$.

FIG. 11B is a graphical representation of the $B_s$-curve being tangent to a T-curve in $D_5$ for the source on $y_1(s)$.

FIG. 11C is a graphical representation of the $B_s$-curve passing across the second T-curve for the source on $y_1(s)$.

FIG. 12A is a graphical representation of the determination of $c_0$.

FIG. 12B is a graphical representation of the determination of $c_1$.

FIGS. 13A-B are respectively graphical representations of filtering lines in the case of $\hat{x} \in G_1 \cup G_3$ and $\hat{x} \in G_2$ for the first fast FBP algorithm.

DETAILED DESCRIPTION OF VARIOUS EMBODIMENTS OF THE INVENTION

Figure 1:
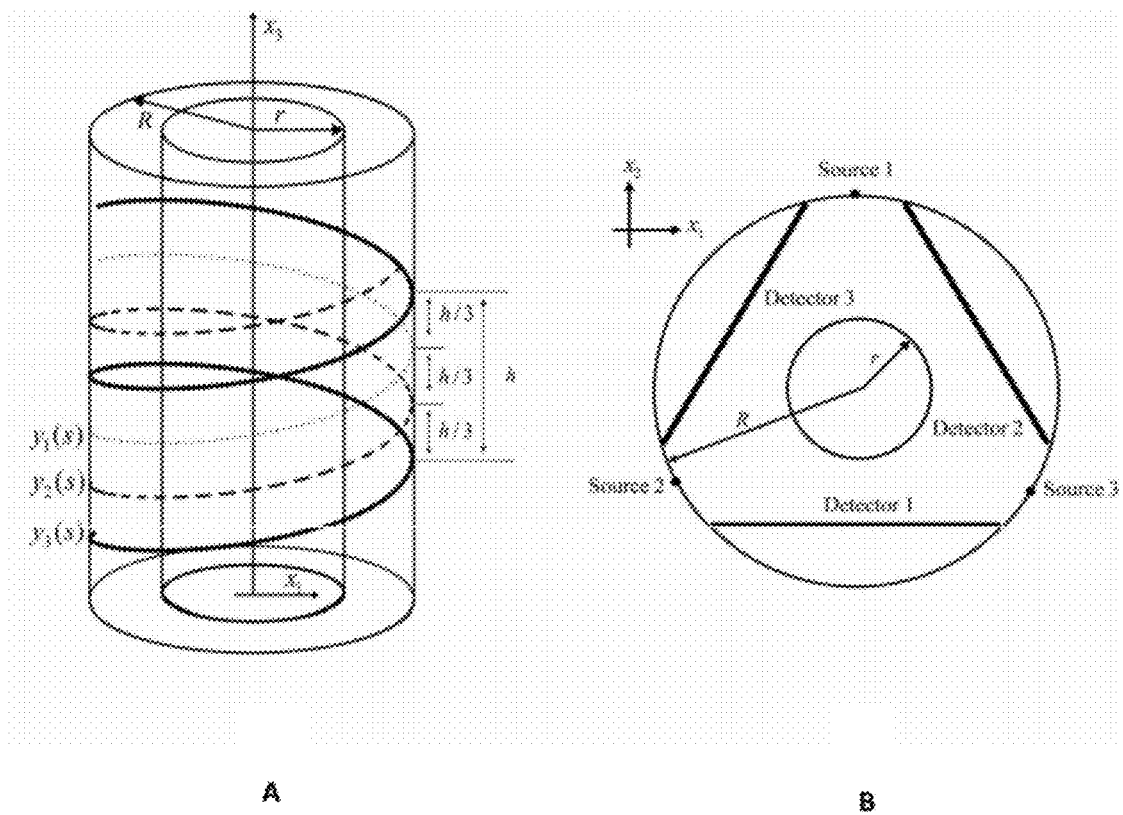
FIGS. 1A-B are schematic diagrams showing geometry of triple-source helical CBCT. Three x-ray sources are rotated around the $x_3$-axis along the helices $y_1(s)$, $y_2(s)$ and $y_3(s)$, respectively. The $y_1(s)$, $y_2(s)$ and $y_3(s)$ are on a cylinder of radius R. An object to be reconstructed is confined within a cylinder of radius r, where r<R. Parameter h denotes the pitch of each helix. The inter-helix distance along the $x_3$-axis is h/3.

In accordance with embodiments of the present invention, a method of the present invention may comprise introducing two fast FBP algorithms for use with conventional cardiac CT technologies in order to obtain better reconstruction images. One of the many potential advantages of the methods of the present invention, only some of which are discussed herein, is that images with less blurring and improved temporal resolution may be obtained even when there is movement in the object being scanned. The current invention may provide benefits to various types of interior tomography including, but not limited to, cardiac, lung, head and neck tomography. In the medical field and in biomedical science, the methods disclosed herein may greatly reduce the production of unusable images and thereby potentially allow increased early detection of diseases, reduced amount of radioactive contrast used on the patients, and/or reduced costs associated with CTs. Better temporal resolution in the images may provide a cost savings by reducing the number of images needed to conclude a finding. This type of scanning may likewise provide more flexibility in designing experiments in small animals in order to better study these diseases and develop effective treatments.

Another potential advantage is that the two fast FBP proposed algorithms utilize the inter-PI line and inter-PI arcs, and have a shift-invariant filtering structure. Unlike our slow-FBP algorithm performing filtration spatial-variantly line by line, the proposed fast-FBP algorithms filter projection data spatial-invariantly view by view, representing a significant computational benefit. Since triple-source helical CBCT may triple temporal resolution, it seems a promising mode for cardiac CT and other CT applications, and our proposed algorithms may find applications in this context. The methods of the present invention allow for temporal resolution in the range of about 100 ms to less than about 10 ms.

Geometry of Triple-Source Helical CBCT.

In particular embodiments, the geometry of the triple-source helical CBCT may be measured by allowing f(x) be an object function to be reconstructed. In embodiments where this function is smooth and vanishes outside the object cylinder EQUATION 1 may be applied as described below:

$$\Omega = \{x = (x_1, x_2, x_3) | x_1^2 + x_2^2 \leq r^2, x_{3min} \leq x_3 \leq x_{3max}\},$$
$$0 < r < R, \quad \text{(EQUATION 1)}$$

where r is the radius of the object cylinder and R the radius of the scanning cylinder on which a scanning trajectory resides. In embodiments with the Cartesian coordinate system ($x_1, x_2, x_3$), the triple-helix trajectories can be expressed as shown in EQUATION 2 below:

$$\begin{cases} y_1(s) = \left(R\cos s, R\sin s, \frac{h}{2\pi}s\right) \\ y_2(s) = \left(R\cos\left(s + \frac{2}{3}\pi\right), R\sin\left(s + \frac{2}{3}\pi\right), \frac{h}{2\pi}s\right) \\ y_3(s) = \left(R\cos\left(s + \frac{4}{3}\pi\right), R\sin\left(s + \frac{4}{3}\pi\right), \frac{h}{2\pi}s\right) \end{cases} \quad \text{(EQUATION 2)}$$

where h>0 is the pitch of each helix, and s∈ℝ is the rotation angle. FIG. 1 illustrates the triple-source helical CBCT geometry.

Figure 2:
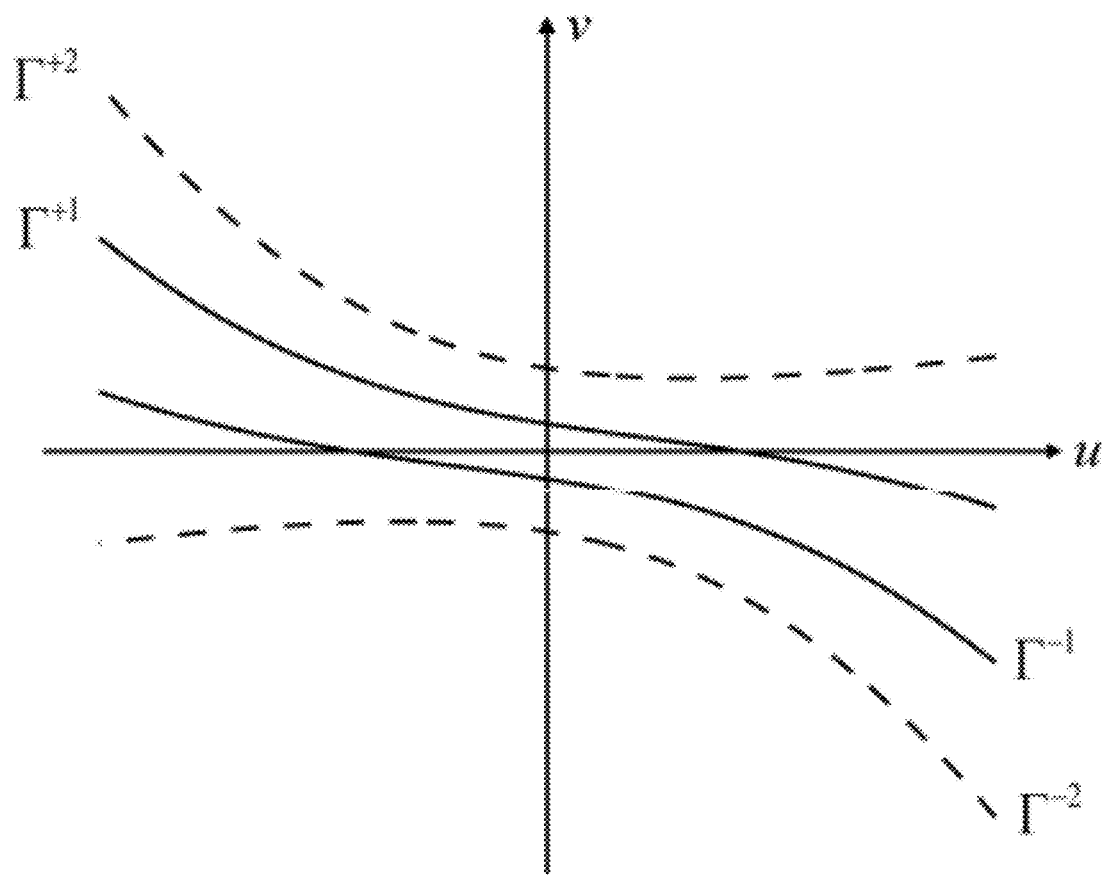
FIG. 2 is an illustration of the Zhao window bounded by solid lines $\Gamma^{\pm 1}$ and the Tam-Danielsson window bounded by dashed lines $\Gamma^{\pm 2}$. The detector plane is represented by the Cartesian coordinate system (u, v).

Previously, the inter-helix PI-lines-were defined and extended the traditional Tam-Danielsson window to the Zhao window in the case of triple helices. The terms inter-helix PI-lines and inter-PI lines are the same and are used interchangeably throughout. Specifically, for each source position $y_j(s)$, j∈ {1, 2, 3}, the corresponding Zhao window is the region on the surface of the scanning cylinder bounded by the nearest helix turn of $y_{jmod3+1}(s)$ and the nearest helix turn of $y_{(j+1)mod3+1}(s)$, j∈ {1, 2, 3}. In FIG. 2, $\Gamma^{\pm 1}$ and $\Gamma^{\pm 2}$ denote the boundaries of the Zhao window and the Tam-Danielsson window on the detector plane, respectively. In certain embodiments, the algorithms described herein are designed for flat-panel detectors. However, in embodiments with detectors of other shapes, the arbitrary-shaped detector may be rebinned to a virtual flat-panel detector in a preprocessing step so that the algorithms of the current disclosure may be used.

The properties of the inter-PI lines and inter-PI arcs may be determined by recalling that an inter-PI line for $y_j(s)$ and $y_{jmod3+1}(s)$, j∈{1, 2, 3}, is the line that (1) intersects $y_j(s)$ at one point and $y_{jmod3+1}(s)$ at another point; and (2) the absolute difference between the angular parameter values at the two intersection points is less than $2\pi$. The existence and uniqueness of the inter-PI line is shown in Theorem 1 below.

Figure 3:
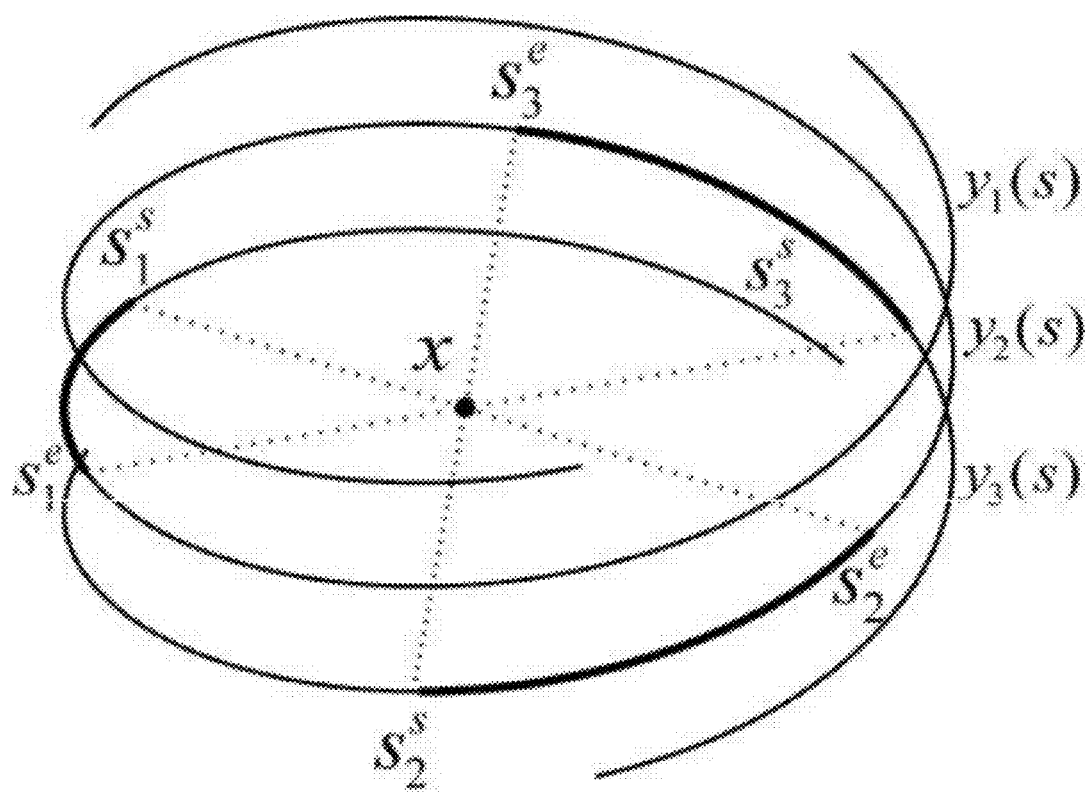
FIG. 3 is a schematic diagram of inter-PI arcs (thick solid curve-arcs).

Theorem 1 states that through any fixed x∈Ω, there exists one and only one inter-PI line for any pair of the three helices defined by EQUATION 2. In the triple-helix case, there are three inter-PI lines for a fixed x∈Ω and corresponding inter-helix PI-arcs whose end points may be along the corresponding helices and share the intersection points of the inter-PI lines. In some embodiments, the three inter-PI arcs represent the source trajectory arcs along which the sources illuminate the point x as shown in FIG. 3.

In 2003, Katsevich proposed a general scheme for constructing inversion algorithms for CBCT. It can be stated as follows in EQUATIONS 3-8:

$$f(x) = \qquad \text{(EQUATION 3)}$$
$$-\frac{1}{4\pi^2}\int_I \sum_m \frac{c_m(s, x)}{|x - y(s)|} \times \int_0^{2\pi} \frac{\partial}{\partial q} D_f(y(q), \cos\gamma\beta(s, x) +$$
$$\sin\gamma\alpha^\perp(s, x, \theta_m))\bigg|_{q=s} \frac{dy}{\sin\gamma} ds$$

$$\beta(s, x) := \frac{x - y(s)}{|x - y(s)|}, \qquad \text{(EQUATION 4)}$$

$$\alpha^\perp(s, x, \theta) := \beta(s, x) \times \alpha(s, x, \theta), \qquad \text{(EQUATION 5)}$$

$$c_m(s, x) := \lim_{\varepsilon \to 0^+} (\phi(s, x, \theta_m + \varepsilon) - \phi(s, x, \theta_m - \varepsilon)), \qquad \text{(EQUATION 6)}$$

$$\phi(s, x, \theta) := \text{sgn}(\alpha \cdot \dot{y}(s))n(s, x, \alpha), \qquad \text{(EQUATION 7)}$$

$$I := \bigcup_{l=1}^{L_c} [a_l, b_l] \to \mathbb{R}^3, I \ni s \to y(s) \in \mathbb{R}^3, \qquad \text{(EQUATION 8)}$$

$$|\dot{y}(s)| \neq 0.$$

where $D_f(y, \beta)$ is the cone-beam transform of f, θ the polar angle in the plane perpendicular to β(s, x), α(s, x, θ) a unit vector perpendicular to β(s, x), $\theta_m$ a point where φ(s, x, θ) is discontinuous, n(s, x, α) a weight function, C a finite union of $C^\infty$ curves in $\mathbb{R}^3$, $-\infty < a_1 < b_1 < \infty$, and $\dot{y}(s):=dy/ds$.

The aforementioned general inversion formula can be applied to any trajectory that satisfies Tuy's condition, but only when the weight function n(s, x, α) is well designed can the inversion formula have a shift-invariant filtering structure. To derive fast exact FBP algorithms for triple-source helical CBCT, our general approach involves the following key concepts of and analyses on the inflection line, A-, T-, L-, and Bs-curves.

Inflection line. On the detector plane, the boundaries of the Zhao window may be expressed as EQUATION 9 below:

$$u(s) = \frac{D\sin s}{1 - \cos s}, \quad v(s) = \frac{Dh}{2\pi R}\frac{(s + \Delta s)}{(1 - \cos s)} \qquad \text{(EQUATION 9)}$$

where D is the distance between the detector and the source, s is the angular parameter relative to the corresponding source position, $\Delta s = -2/3\pi$ and $\Delta s = -4/3\pi$ are for the top and bottom boundaries respectively. Then, EQUATIONS 10-14 can be used.

$$\dot{u}(s) = \frac{D}{\cos s - 1}, \qquad \text{(EQUATION 10)}$$

$$\ddot{u}(s) = \frac{D\sin s}{(\cos s - 1)^2}, \qquad \text{(EQUATION 11)}$$

$$\dot{v}(s) = \frac{Dh}{2\pi R}\frac{[1 - \cos s - (s + \Delta s)\sin s]}{(1 - \cos s)^2}, \qquad \text{(EQUATION 12)}$$

$$\ddot{v}(s) = \frac{Dh}{2\pi R}\frac{(\cos s - 1)(s + \Delta s)\cos s + 2\sin s(\cos s + s\sin s + \Delta s\sin s - 1)}{((1 - \cos s)^3)}, \qquad \text{(EQUATION 13)}$$

$$\frac{d^2 v}{du^2} = \frac{\ddot{v}(s)\dot{u}(s) - \ddot{u}(s)\dot{v}(s)}{[\dot{u}(s)]^3} = \frac{h}{2\pi D}(s + \Delta s - \sin s). \qquad \text{(EQUATION 14)}$$

The inflection point exists when $$\frac{d^2 v}{du^2} = 0.$$

Thus, we obtain $s_u$=2.6053 and $s_d$=3.6779 when $\Delta s=-2/3\pi$ and $-4/3\pi$. The slope of the tangent line at s can be computed as shown in EQUATION 15 below:

$$\frac{dv}{du} = \frac{\dot{v}(s)}{\dot{u}(s)} \qquad \text{(EQUATION 15)}$$
$$= \frac{h[1 - \cos s - (s + \Delta s)\sin s]}{2\pi R(\cos s - 1)}$$
$$= \frac{h}{2\pi R}\cos s.$$

Figure 4:
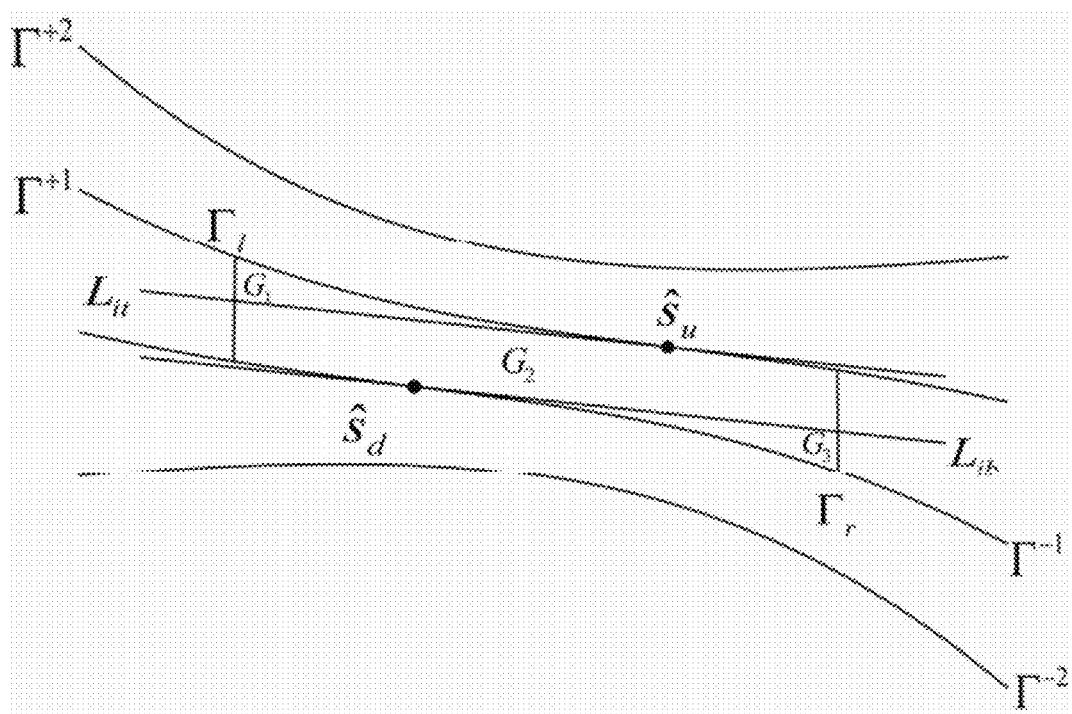
FIG. 4 is a schematic diagram of the decomposition of the Zhao window into the regions $G_1$, $G_2$ and $G_3$. $L_{it}$ and $L_{ib}$ are the inflection lines at $\hat{s}_u$ and $\hat{s}_d$, respectively.

Because cos $s_u$=cos $s_d$=−0.8596, the slope is the same (−0.1368 h/R) at both inflection points. For practical medical applications, it is common that $r_{FOV} \leq 0.5$ R, and a boundary limitation $x_1^2 + x_2^2 \leq r^2$ (r=0.495 R) may be included, which is shown as the vertical lines $\Gamma_l$ and $\Gamma_r$ in FIG. 4. Now, the inflection lines (the tangent lines at $\hat{s}_d$ and $\hat{s}_u$, where $\hat{s}_d$ and $\hat{s}_u$ are the projection of $y_{(j+1)mod3+1}(s_d)$ and $y_{jmod3+1}(s_u)$, $j \in \{1, 2, 3\}$ on the detector plane) and the boundary lines split the Zhao window into the following three regions: $G_1$, $G_2$ and $G_3$. Only the points in $G_1$ and $G_3$ can have tangent lines with $\Gamma^{\pm 1}$.

A-Curve and T-Curve.

To construct an appropriate weight function, the understanding of how Radon planes intersect with the trajectories is important. The number of intersection points only changes when a Radon plane is tangent to the trajectory or contains one PI line/inter-PI line. Hence, if we find all such Radon planes, we can determine the distribution of the intersection points. Since each plane is uniquely determined by its normal vector, in the following sections we use unit vectors instead of the Radon planes. An A-curve consists of all unit vectors orthogonal to an inter-PI line. A T-curve consists of all unit vectors in EQUATION 16 as shown below:

$$\alpha(s) = \pm \frac{(x - y(s)) \times \dot{y}(s)}{|(x - y(s)) \times \dot{y}(s)|}, \quad \text{(EQUATION 16)}$$

where s belongs to an inter-PI arc. Actually, the A-curve represents all Radon planes containing one inter-PI line, and the T-curve represents all Radon planes tangent to the trajectory. Since there are three inter-PI lines and three inter-PI arcs for a fixed x, there are accordingly three A-curves and three T-curves. The use of spherical coordinates $(\theta_1, \theta_2)$ to describe these curves on the unit sphere is shown in EQUATION 17:

$$\alpha = (\cos\theta_1 \sin\theta_2, \sin\theta_1 \sin\theta_2, \cos\theta_1), -\pi \leq \theta_1 \leq \pi,$$
$$0 \leq \theta_2 \leq \pi. \quad \text{(EQUATION 17)}$$

With the identification $(\theta_1, \theta_2) \equiv ((\theta_1+\pi)_{mod 2\pi}, \pi-\theta_2)$, each $\alpha$ corresponds to a unique plane through x with the normal vector $\alpha$.

Figure 5:
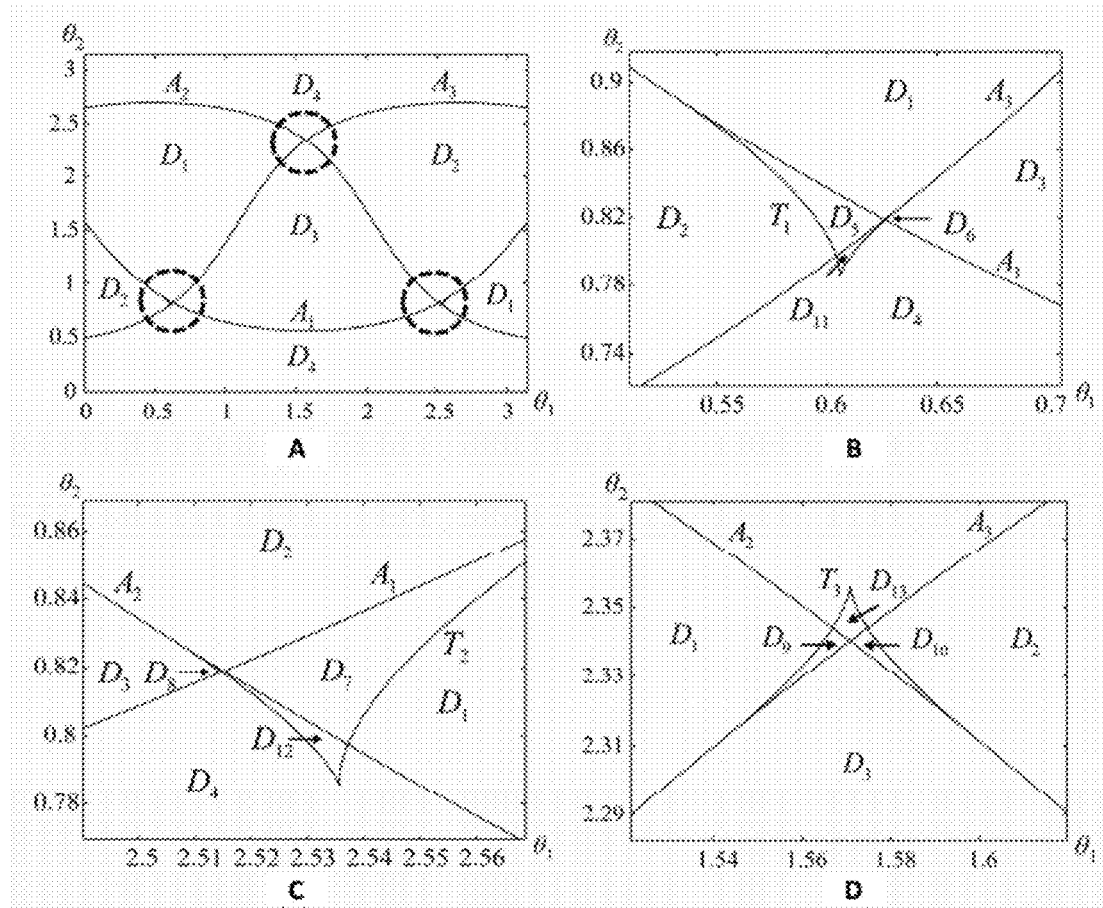
FIG. 5A is a graphic representation allowing for the visualization of the domains delimited by the A-curves and T-curves on the surface of the unit sphere in spherical coordinates for x=(0.1, 0, 0).
FIGS. 5B, C, and D are graphic representations of the zoom-in versions of the areas bounded by the bottom left, bottom right, and top circles shown in FIG. 5A, respectively.

As an example, the A-curves and T-curves of point x=(0.1, 0, 0) are illustrated in FIG. 5, where R=1, h=2π. $T_1$, $T_2$ and $T_3$ stand for the T-curves corresponding to the inter-PI arcs $\widehat{S_1^e S_1^e}$, $\widehat{S_2^e S_2^e}$ and $\widehat{S_3^e S_3^e}$ respectively. Similarly, $A_1$, $A_2$ and $A_3$ are for the A-curves corresponding to the inter-PI lines $\overline{s_1^s s_2^e}$, $\overline{s_2^s s_3^e}$ and $\overline{\hat{s}_1^e \hat{s}_3^e}$ respectively.

The A-curves and T-curves may divide the surface of the unit sphere into several connected domains, in each of which all the planes through x have the same number of intersection points (IPs) with the inter-PI arcs of x. Given an object point and one trajectory, the number of IPs only changes when a Radon plane is tangent to the trajectory or contains the endpoints of the trajectory. The A-curve represents all planes containing the endpoints of the trajectory, and the T-curve represents all planes tangent to the trajectory. If any Radon plane is chosen and rotated around one direction, the normal vector of this plane forms a curve on the unit sphere. Clearly, only when this curve intersects with the A-curve or T-curve does the number of IPs change. Thus, the A-curve and T-curve define the boundaries of different domains in which the number of IPs is constant. The distribution of IPs over the inter-PI arcs is listed in Table I. To determine the distribution of IPs, we first pick a vector $\alpha(\theta_1, \theta_2)$ in each domain, and then generate the plane through x and perpendicular to $\alpha(\theta_1, \theta_2)$, and compute numerically the number of IPs.

TABLE I

Distribution of IPs on Each of the Domains Delimited by the A-curves and T-curves on the Surface of the Unit Sphere. The dash indicates no IP on the corresponding inter-PI arc.

|  | $\widehat{S_1^e S_1^e}$ | $\widehat{S_2^e S_2^e}$ | $\widehat{S_3^e S_3^e}$ |
|---|---|---|---|
| $D_1$ | 1 | — | — |
| $D_2$ | — | 1 | — |
| $D_3$ | — | — | 1 |
| $D_4$ | 1 | 1 | 1 |
| $D_5$ | 2 | 1 | — |
| $D_6$ | 2 | — | 1 |
| $D_7$ | 1 | 2 | — |
| $D_8$ | — | 2 | 1 |
| $D_9$ | 1 | — | 2 |
| $D_{10}$ | — | 1 | 2 |
| $D_{11}$ | 3 | 1 | 1 |
| $D_{12}$ | 1 | 3 | 1 |
| $D_{13}$ | 1 | 1 | 3 |

Figure 6:
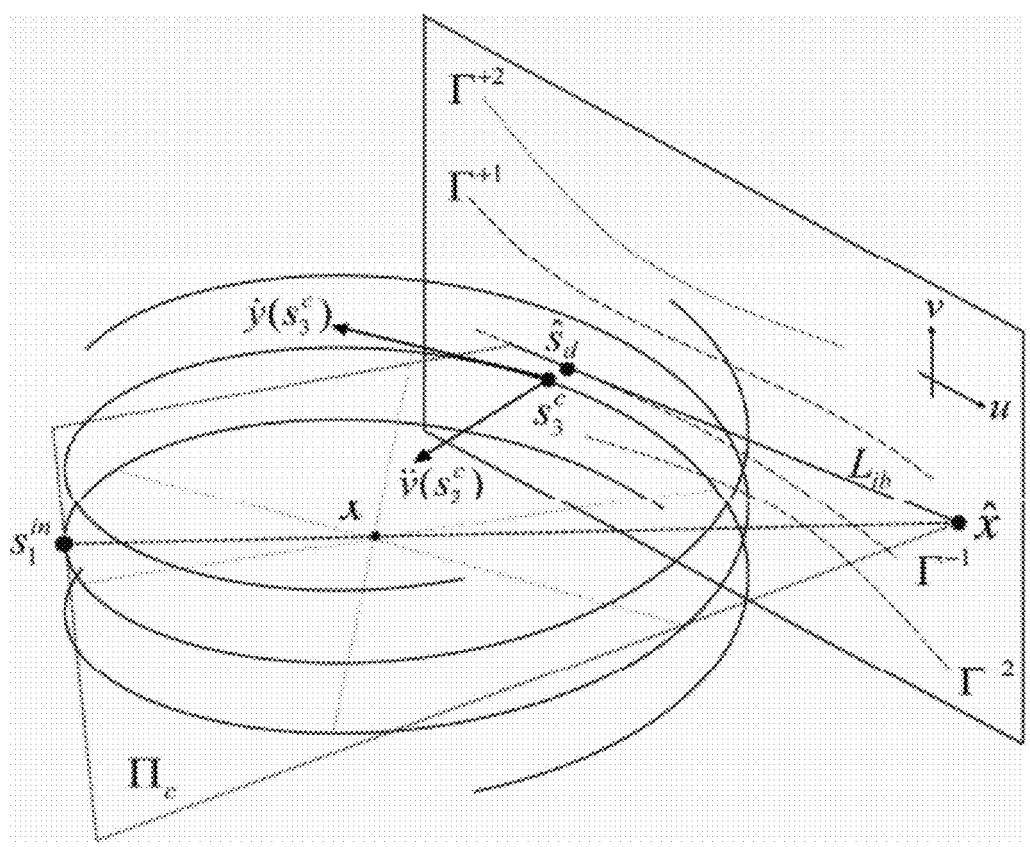
FIG. 6 is an illustration of the osculating plane $\pi_c$.

By construction, a T-curve always starts from an A-curve and ends on another A-curve. It can be seen from FIG. 5 that a T-curve is may not be smooth at some point $a_c$, but the limits of unit tangent vectors at $a_c^-$ and $a_c^+$ are equal Such a point $a_c$ is defined herein as a "cusp". The term cusp indicates that the two vectors determine the same plane, and $a_c$ is the normal vector to that plane. It has been proved in that the cusp is equivalent to the osculating plane $\Pi_c(x)$ which goes through $y_1(s_1^c(x))$ i$\in$\{1, 2, 3\}, is parallel to $\dot{y}_1(s_1^c(x))$, $\ddot{y}_1(s_1^c(x))$ and contains x (see FIG. 6). On the detector plane, this corresponds to a point where the projected boundary has a point of zero curvature, i.e., the point of inflection.

The diagram plotted in spherical coordinates deforms smoothly as a function of x. The new diagram is equivalent to the old one in the embodiments where the distribution of IPs remain the same. An essential change could happen when three boundaries intersect each other at one point, which is defined herein as a "critical event". The term "critical event" may happen in the following seven cases:

1. Three A-curves intersect at one point;
2. Three T-curves intersect at one point.
3. Two A-curves and one T-curve intersect at one point;
4. One A-curve and two T-curves intersect at one point;
5. A T-curve becomes tangent to an A-curve at a point of non-smoothness (i.e., cusp);
6. When the order of tangency (i.e., the zero derivatives of this order) at the beginning of the T-curve is increased, the T-curve re-emerges on the other side of the A-curve;
7. T-curve develops a smooth dent and becomes-tangent to an A-curve.

Figure 7:
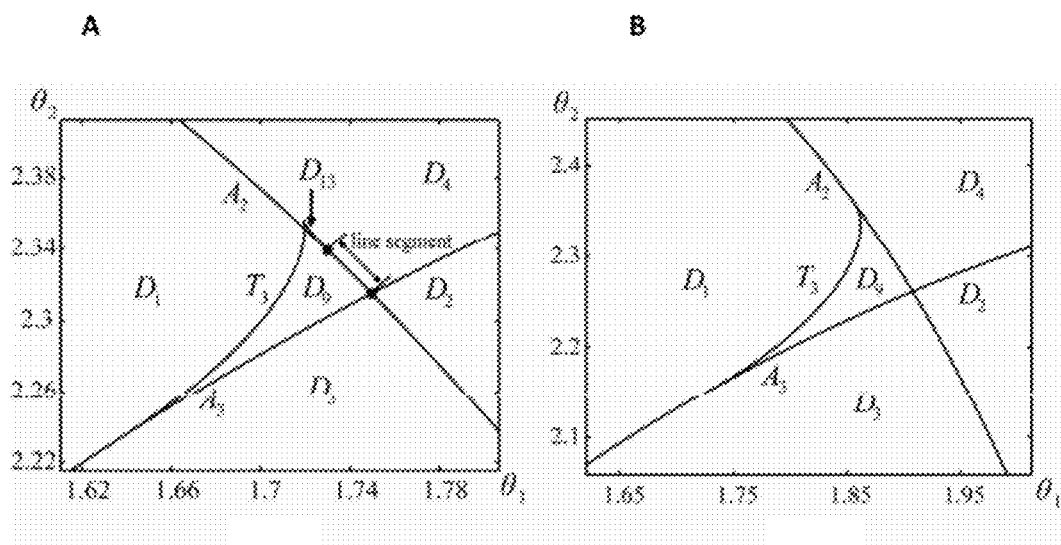
FIGS. 7A and B are graphical representations of the close-up views of the diagram for x=(0, −0.15, 0) for 7A and x=(0, −0.3, 0) for 7B.

From Lemmas 2-3 described below in the Examples section, it is shown that Cases 1, 2, 4, 6, 7 do not occur for r<0.495 R and Case 5 does not occur for r<0.265 R. In some embodiments, Case 3 is possible. In embodiments where Case 3 takes place, the tangency of T-curve and A-curve will move across another A-curve, then one domain disappears. For example, when x=(0.1, 0, 0) gradually changes to x=(0, −0.15, 0), in FIG. 5D the tangency of $T_3$ and $A_2$ will move across $A_3$, and domain $D_{10}$ disappears (see FIG. 7A). In other embodiments, Case 5 is possible for r≧0.265 R. In these embodiments, a T-curve will only intersect A-curves at the endpoints. That is, the cusp of that T-curve and one domain disappear (see FIG. 7B).

L-Curve.

Figure 8:
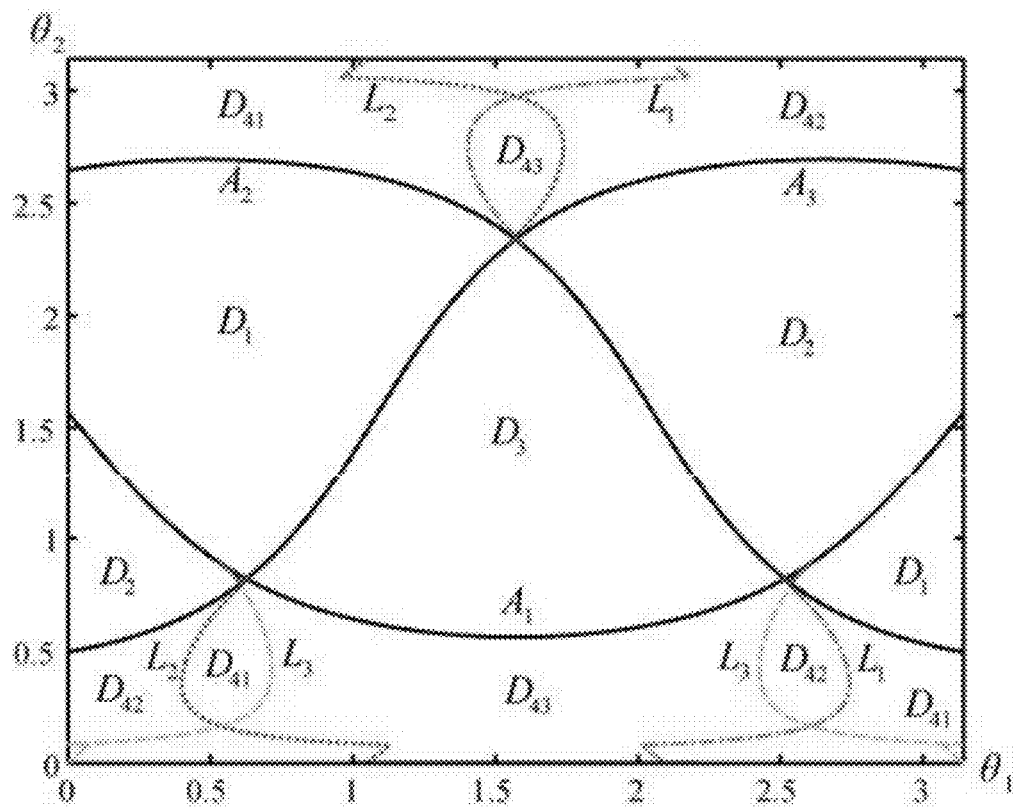
FIG. 8 is a graphical illustration of L-curves in the spherical coordinates $\theta_1, \theta_2$).

The L-curve may be used to split the domain $D_4$ into subdomains, making the weight function n continuous across all the A-curves. This is the key requirement, which may allow for the development of efficient reconstruction algorithms. Thus, the L-curve should not go across an A-curve. In embodiments where x is fixed and s is run over the three inter-PI arcs, $\hat{x}$ forms a trajectory on the detector plane. Because at the endpoint of the inter-PI arc the line connecting $y_i(s)$ and x happens to be an inter-PI line, $\hat{x}$ always starts from one endpoint of the inter-PI arc on the boundary of the Zhao window, and ends at the other one. Hence, whatever the trajectory of $\hat{x}$ is, part of the trajectory is in $G_2$. In other words, $\hat{x}$ will run across one inflection line, then move in $G_2$, and finally cross the other inflection line. Note that $\hat{x}$ on the inflection line indicates a plane containing the inflection line, i.e., a cusp in one T-curve. From Lemma 3 described in the Example section below, the cusps always belong to the boundary of domain $D_4$. Thus, they can be used as the endpoints of the L curve. A family of L-curves is formed as follows. Run s over the three inter-PI arcs of x. If $\hat{x}$ is in $G_2$ and above $\hat{s}_u$ where $\Gamma^{+1}$ intersects $L_{it}$ (FIG. 4), find the plane through $\hat{x}$ and $\hat{s}_u$. If $\hat{x}$ is in $G_2$ and below $\hat{s}_d$ where $\Gamma^{-1}$ intersects $L_{ib}$, find the plane through $\hat{x}$ and $\hat{s}_d$. If $\hat{x}$ is in $G_2$ and between $\hat{s}_d$ and $\hat{s}_u$, find the plane through $\hat{x}$ and parallel to the u-axis. A plot of all the normal unit vectors of these planes in the spherical coordinates $(\theta_1, \theta_2)$ may then be constructed. This gives us three L-curves. The corresponding lines on the detector plane are called L-lines. FIG. 8 shows the L-curves on the diagram in spherical coordinates $(\theta_1, \theta_2)$, where $L_1$, $L_2$ and $L_3$ denote the L-curves corresponding to the inter-PI arcs $\widehat{S_1^c S_1^e}$, $\widehat{S_2^c S_2^e}$ and $\widehat{S_3^c S_3^e}$ respectively. As is seen from the above construction, the L-curve always starts and ends on the cusps, and not defined for those parameter values when $\hat{x}$ is not in $G_2$.

Figure 9:
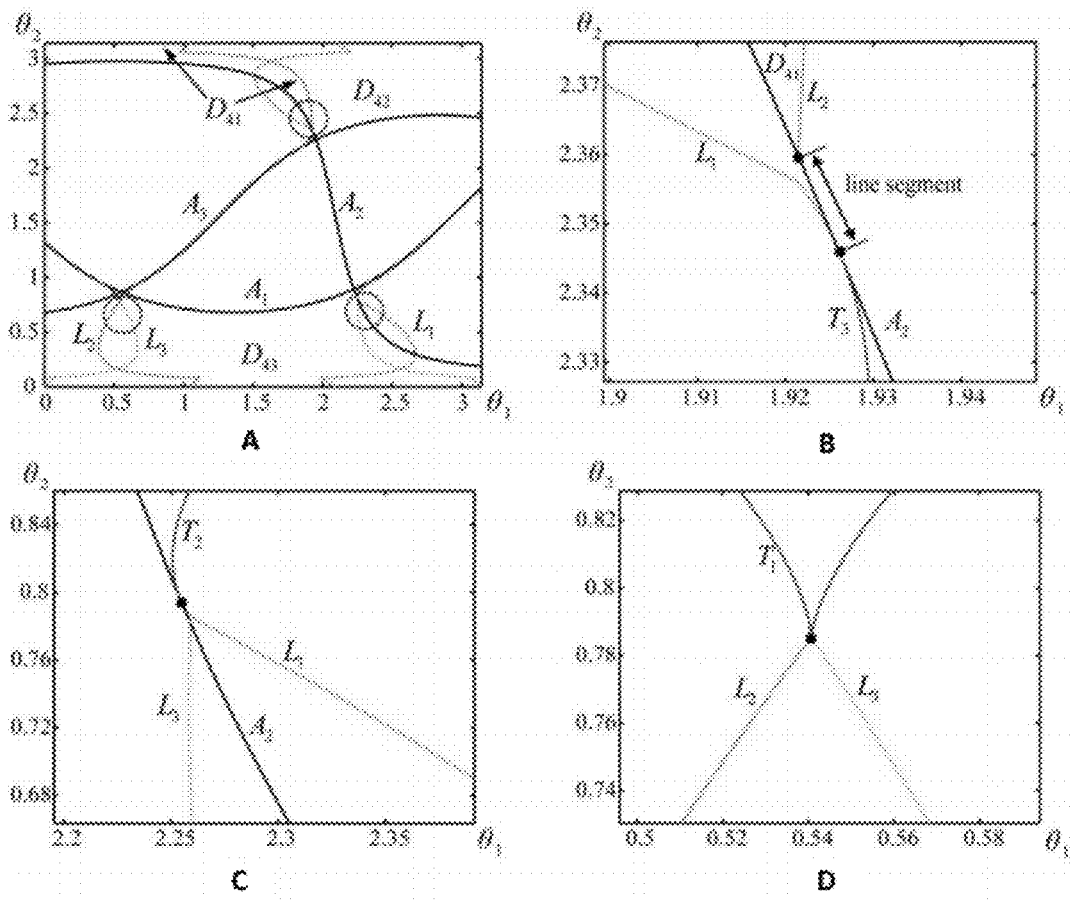
FIG. 9A is a graphic representation of the full diagram showing different regions split by A-, T- and L-curves for L-curves in x=(0.2, −0.3, 0).
FIGS. 9B, C, and D are graphic representations of the zoom-in versions of the regions bounded by the upper, bottom right, and bottom left circles shown in FIG. 9A.

For $r \geq 0.265$ R, one or more cusps will disappear if "critical event Case 5" occurs, then the L-curve may start from the intersection of T-curve and A-curve, and end at one A-curve. Also, the L-curve may start from one cusp and end at one A-curve or start from the intersection of T-curve and A-curve, and end at one A-curve. For example, see FIG. 9, $L_1$ starts from the intersection of $T_3$ and $A_2$, and ends at the intersection of $T_2$ and $A_2$; $L_2$ starts from one point on $A_2$, and ends at the cusp of $T_1$; $L_3$ starts from the cusp of $T_1$, and ends at one point on $A_2$.

Whatever the endpoints of L-curves are, the L-curves intersects at one point, for example, in some embodiments, $\theta_2 = \pi$ or 0 in the spherical coordinates (which corresponds to the plane containing x and parallel to the $x_1$-$x_2$ plane). Then $D_4$ is split into several sub-domains. If the endpoints of L-curves are cusps, by Lemma 5, each sub-domain contains only one A-curve. If not, small "line segments" on A-curves may appear and the sub-domains may contain more than one A-curve (see FIG. 9B).

Figure 10:
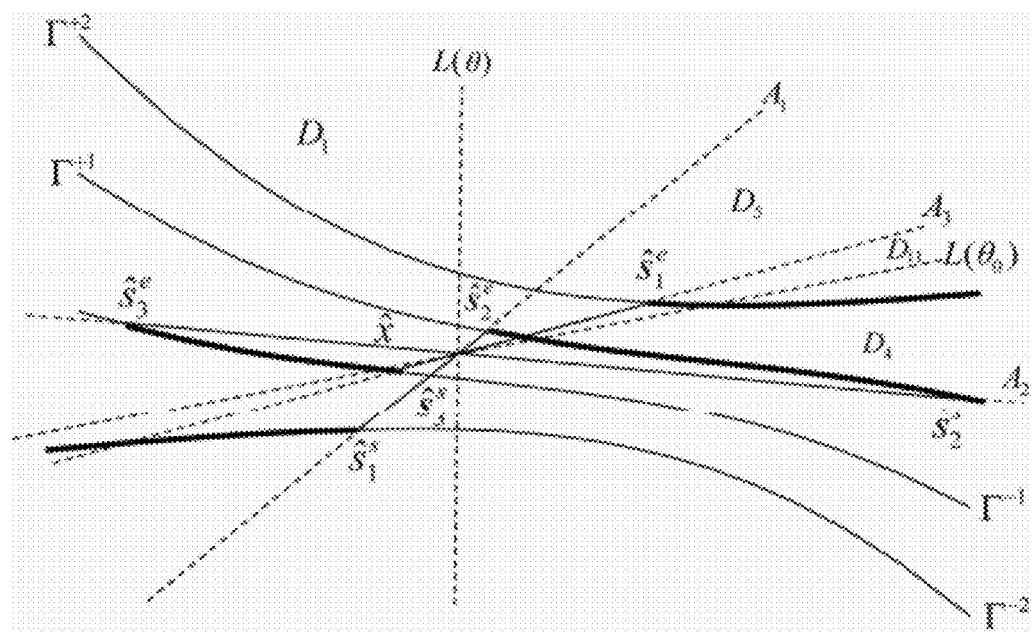
FIG. 10 is a graphic representation of domains on the detector plane.

$B_s$-curve. A $B_s$-curve may consist of all unit vectors perpendicular to $x$-$y_i(s)$, $i \in \{0, 2, 3\}$. Each intersection of $B_s$- and A-curves corresponds to a plane containing an inter-PI line and $y_i(s)$. Each intersection of B, and T-curves corresponds to a plane tangent to an inter-PI arc and containing $y_i(s)$. For example, in certain embodiments, one may choose $x \in \Omega$ with $\hat{x} \in G_2$, $\hat{x}$ is above $L_0$, where $L_0$ is the projection of the helical tangent at the current position. If $L(\theta) := DP(s) \cap \Pi(x, \alpha(s, x, \theta))$ is denoted, where $DP(s)$ is the detector plane corresponding to the source position s, and $L(\theta)$ is the projection of the plane through x with the normal vector $\alpha(s, x, \theta)$ (FIG. 10), then as $\theta$ increases, $\alpha(s, x, \theta) \in \beta^L(s, x)$ rotates clockwise on $DP(s)$, and the following sequence of events takes place. First, $\Pi(x, \alpha(s, x, \theta))$ intersects $\widehat{\hat{s}_1{}^s \hat{s}_2{}^c}$, and a pair of IPs is born. On the unit sphere, this is seen as an intersection of $B_s$ and $A_1$, after which $B_s$ enters $D_5$ (FIG. 11a). Second, $\Pi(x, \alpha(s, x, \theta))$ intersects $\widehat{\hat{s}_3{}^s \hat{s}_1{}^c}$ and another pair of IPs is born. On the unit sphere, this is seen as an intersection of $B_s$ and $A_3$, after which $B_s$ enters $D_{11}$. Third, a swap of two IPs takes place. On $DP(s)$ this happens when $\theta = \theta_0$, $L(\theta_0)$ is parallel to the helical tangent. On the unit sphere, this means that $B_s$ is tangent to $T_1$ at $\alpha_0 = \alpha(s, x, \theta_0)$. Fourth, $B_s$ exits $D_{11}$ by intersecting $T_1$. On $DP(s)$, this takes place when $L(\theta)$ is tangent to $\Gamma^{+2}$. Finally, $\Pi(x, \alpha(s, x, \theta))$ intersects the L-line. This will not change the number of IPs but it will be useful for construction of the weight function. On the unit sphere, this is seen as an intersection of $B_s$ and $L_1$.

Figure 14:
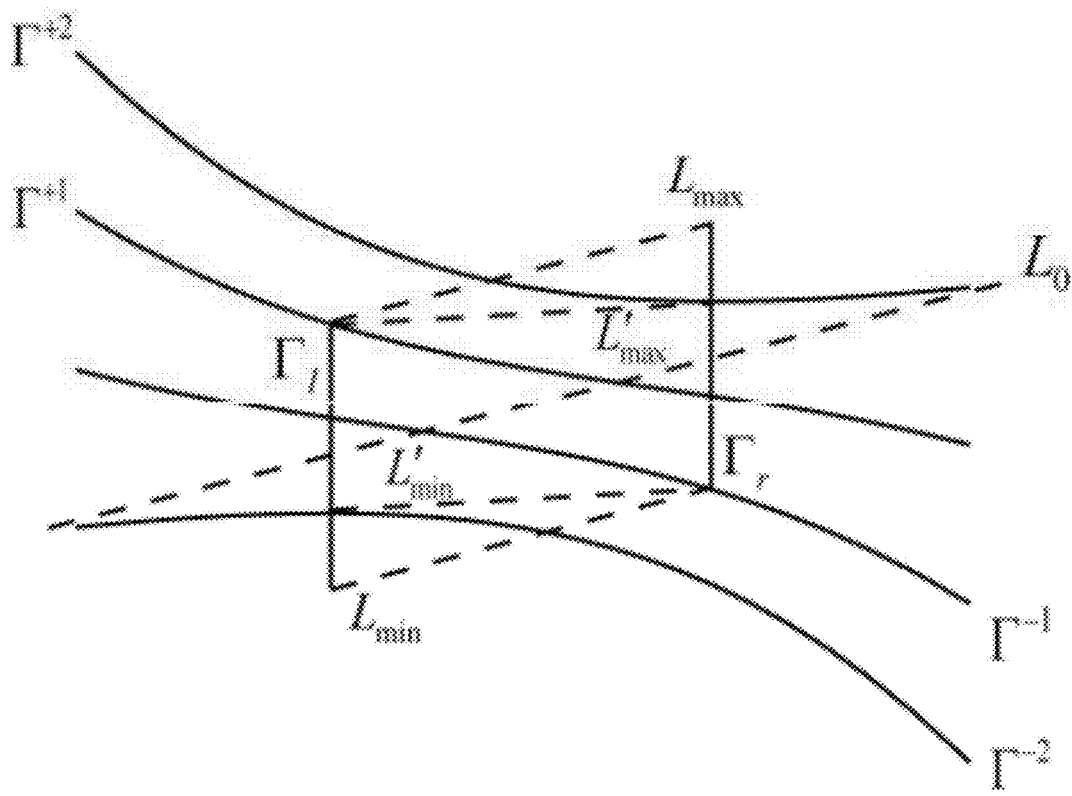
FIG. 14 is a graphical representation showing that the required detector area is bounded by $\Gamma_t, \Gamma_l, L_{max}$ and $L_{min}$ for the first algorithm, and by $\Gamma_t, \Gamma_l, L'_{max}$ and $L'_{min}$ for the second algorithm.

The jumps across an A-curve can only be of two types: from a 1-IP domain to a 3-IP domain and from a 3-IP domain to a 5-IP domain. Note that the $B_s$-curve is tangent from the inside to $T_1$, which means a swap of two intersection points at $\alpha = \alpha_0$ where $\text{sgn}(\alpha_0 \cdot \dot{y}(s)) = 0$ (see [15]). For a fixed s, if x is allowed to change slightly inside the Zhao window, the tangency point will move from $D_{11}$ to $D_5$ across $A_3$ (or from $D_{11}$ to $D_6$ across $A_1$) (FIGS. 12-13). If x projects into $G_1$ or $G_3$, the $B_s$-curve will pass not only through $D_5$ (or $D_6$) and $D_{11}$ but also through $D_7$ and $D_{12}$ (FIG. 14). The similar results can be obtained if the source is on $y_2(s)$ or $y_3(s)$.

Two filtered-backprojection algorithms for triple-source helical cone-beam CT can be used to obtain images having higher temporal resolution. The first exemplary algorithm uses two families of filtering lines, which are parallel to the tangent of the scanning trajectory and the so-called L lines. The second algorithm uses two families of filtering lines tangent to the boundaries of the Zhao window and L lines, respectively, but it eliminates the filtering paths along the tangent of the scanning trajectory, thus reducing the detector size greatly. Additional information concerning these algorithms can be found in Lu, Yang, et al., "Fast Exact/Quasi-Exact FBP Algorithms for Triple-Source Helical Cone-Beam CT," IEEE Transactions on Medical Imaging, Vol. 29, No. 3, March 2010, which is incorporated by references herein in its entirety.

First Fast FBP Algorithm.

In order to design an algorithm for triple-source helical CBCT useful in cardiac CTs and other CTs where movement exists, the weight function $n(s, x, \alpha)$ must be specified. The filtering directions by the discontinuities of $\phi(s, x, \theta) := \text{sgn}(\alpha \cdot \dot{y}(s)) n(s, x, \alpha)$ must also be determined. Following the determination of the filtering directions, the backprojection coefficients can be calculated according to EQUATION 6. Once the filtering lines and the backprojection coefficients are determined, EQUATION 3 may be used to reconstruct the object.

In order to construct the weight function $n(s, x, \alpha)$ one should know the following. In certain embodiments, in order to have an efficient FBP structure, the weight function $n(s, x, \alpha)$ should be continuous across all A-curves. Thus, the weight function can be defined as shown in Table II. The values in Table II are the weights assigned to IPs. For example, in the $D_1$ domain the Radon plane has only one IP on the inter-PI segment $\widehat{S_1^c S_1^e}$. Accordingly, a weight of 1 may be assigned to this IP and a dash used to indicate that there is no IP on the inter-PI segments $\widehat{S_2^c S_2^e}$ and $\widehat{S_3^c S_3^e}$. In the $D_{11}$ domain the Radon plane has three IPs on $\widehat{S_1^c S_1^e}$, one IP on $\widehat{S_2^c S_2^e}$ and one IP on $\widehat{S_3^c S_3^e}$. Thus, a weight of $-1$ may be assigned to two IPs on $\widehat{S_1^c S_1^e}$ and a weight of 1 to all other IPs.

TABLE II

Weight Function for the First Fast FBP Algorithm

| | $\widehat{S_1^*S_1^*}$ | $\widehat{S_2^*S_2^*}$ | $\widehat{S_3^*S_3^*}$ |
|---|---|---|---|
| $D_1$ | +1 | — | — |
| $D_2$ | — | +1 | — |
| $D_3$ | — | — | +1 |
| $D_5$ | +1, 0 | 0 | — |
| $D_6$ | +1, 0 | — | 0 |
| $D_7$ | 0 | +1, 0 | — |
| $D_8$ | — | +1, 0 | 0 |
| $D_9$ | 0 | — | +1, 0 |
| $D_{10}$ | — | 0 | +1, 0 |
| $D_{11}$ | +1, 0, 0 | 0 | 0 |
| $D_{12}$ | 0 | +1, 0, 0 | 0 |
| $D_{13}$ | 0 | 0 | +1, 0, 0 |
| $D_{41}$ | +1 | 0 | 0 |
| $D_{42}$ | 0 | +1 | 0 |
| $D_{43}$ | 0 | 0 | +1 |

To find the backprojection coefficients, a representative point in each area is selected in order to determine the discontinuities of $\phi(s, x, \theta) := \text{sgn}(\alpha \cdot y(s))n(s, x, \alpha)$ and extend the results by continuity to the entire area. A discontinuity of sgn occurs only when a $B_s$-curve is tangent to a T-curve from the inside. In other words, the $B_s$-curve does not go across the T-curve, but stays on one side in a neighborhood of the point of tangency. On the detector plane, $L(\theta)$ is parallel to the helical tangent for all $\hat{x} \in G_1 \cap G_2 \cap G_3$. Hence, this gives a family of filtering lines parallel to $L_0$, where $L_0$ is the projection of the helical tangent at $y(s)$. The swap of two IPs changes the weight from n=0 to n=1. The backprojection coefficient is computed as $c_0 = \phi^+ - \phi^- = (+1)(0) - (-1)(1) = 1$ (FIG. 12A).

Figure 15:
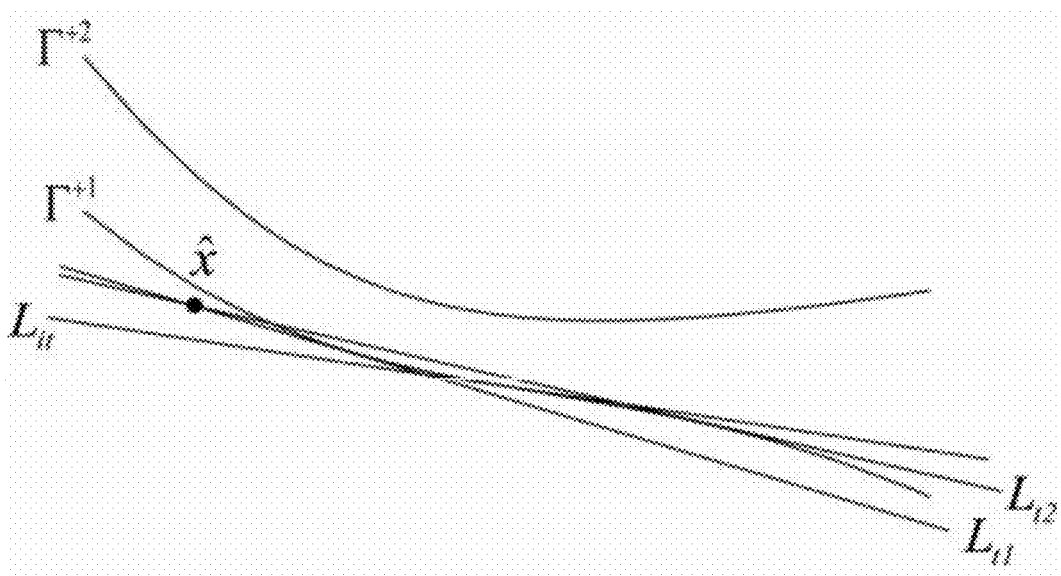
FIG. 15 is a graphical representation of filtering lines for two fast FBP algorithms when $\hat{x}$ is above where $L_{t1}, L_{t2}$, and $L_{r1}$ are for the first and second algorithms, respectively.
Figure 16:
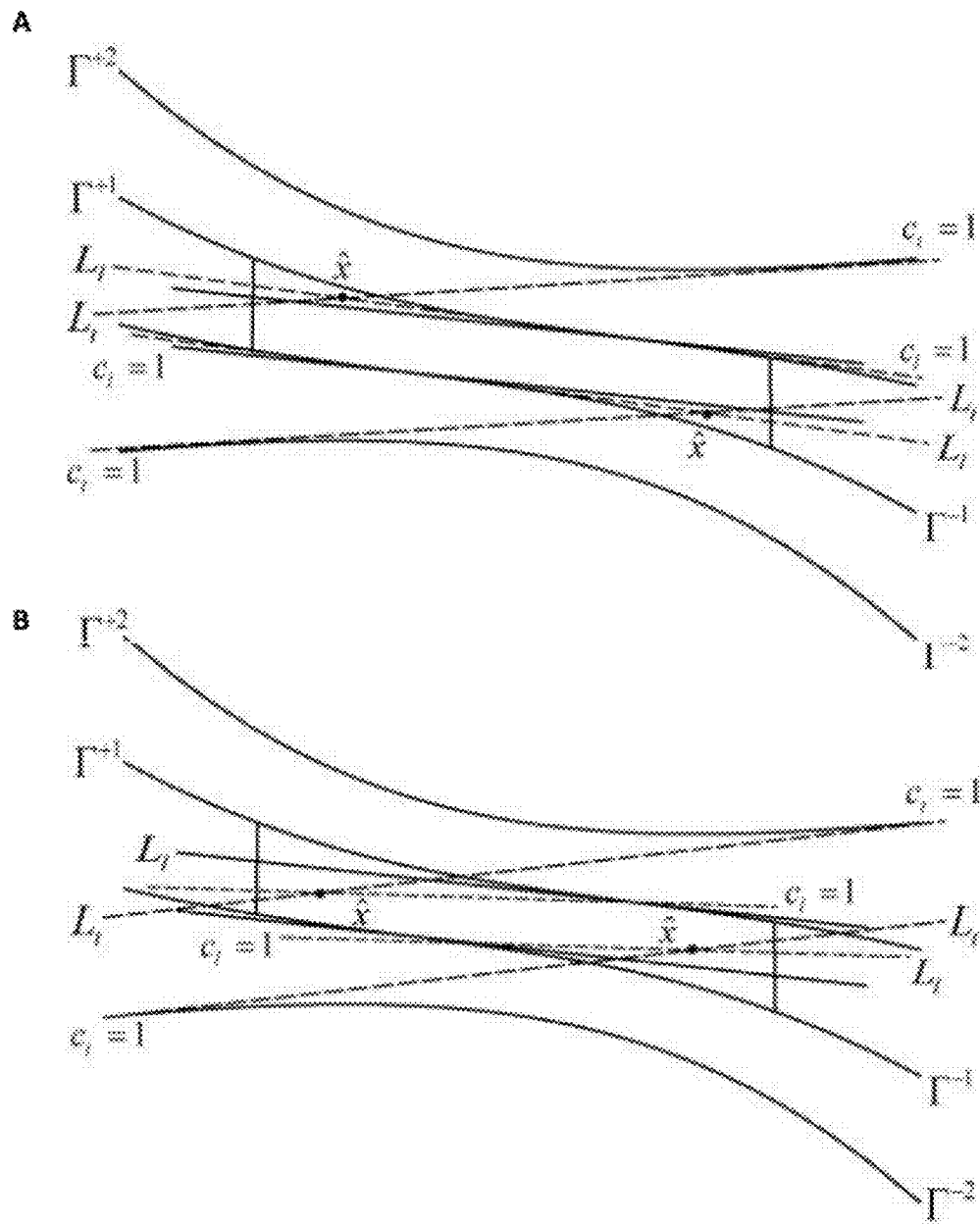
FIGS. 16A and 16B are graphical representations illustrating the second fast FBP algorithm.
Figure 17:
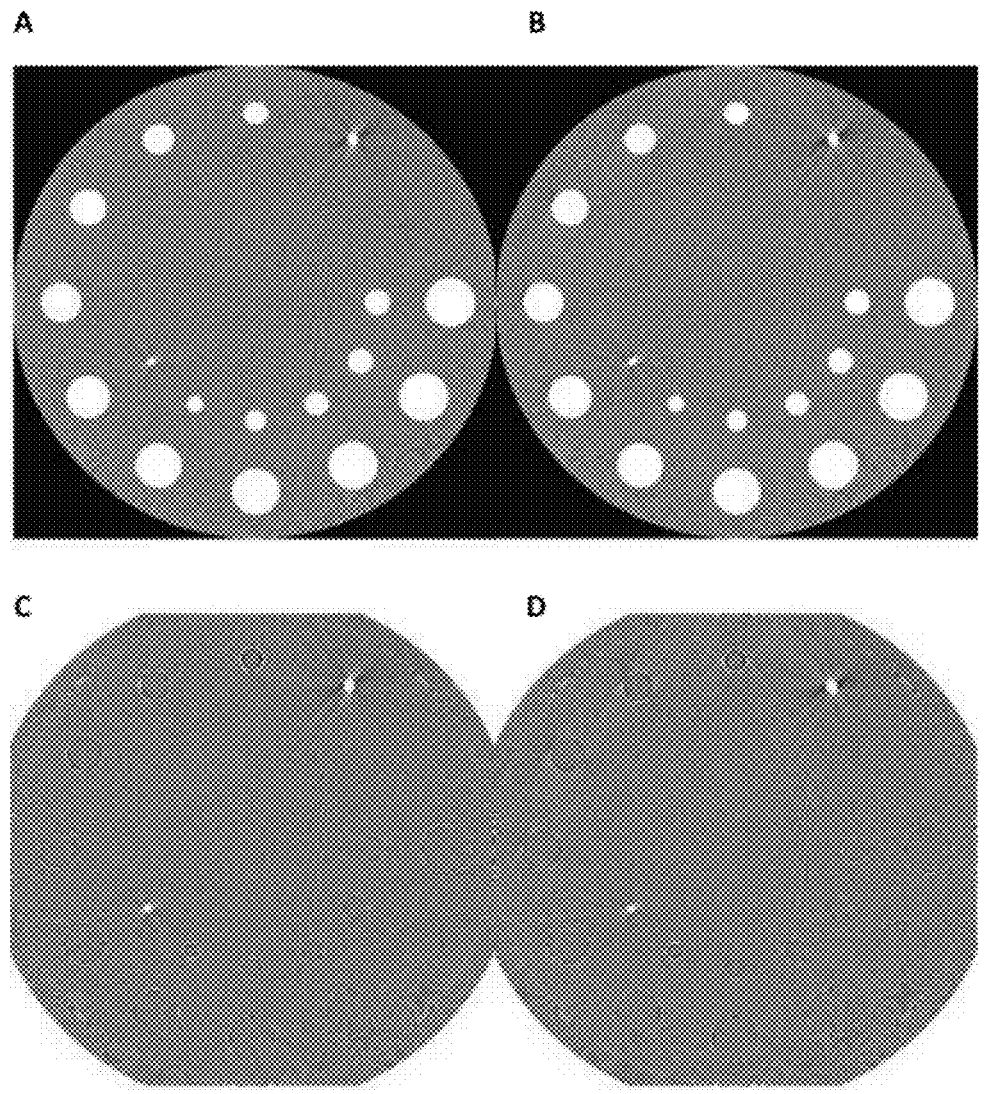
FIG. 17A is a reconstructed image of the Clock phantom with r=375 mm using the first fast FBP algorithm.
FIG. 17B is a reconstructed image of the Clock phantom with r=375 mm using the second fast FBP algorithm.
FIGS. 17C and D are images representing the differences between the reconstructed images in FIGS. 17A and 17B and the ground truth respectively in the display window [−0.5, 0.5].

In certain embodiments, by construction, the weight function n is continuous across all inter-PI lines. A discontinuity of n occurs only when a $B_s$-curve intersects a T-curve or an L-curve. Without loss of generality or wishing to be limited by theory, choosing $y_1(s_0)$ on $\widehat{S_1^*S_1^*}$. For $\hat{x} \in G_2$, after the swap mentioned in the above paragraph the weight at the current position is zero. Hence, when the $B_s$-curve passes through a T-curve, i.e., from $D_{11}$ to $D_4$, n is continuous. Possible jumps of n may only occur when a $B_s$-curve passes through an L-curve, i.e., from $D_{43}$ to $D_{41}$ or from $D_{42}$ to $D_{41}$ in FIG. 8. On the detector plane, this occurs when $L(\theta)$ overlaps the L-line of $\hat{x}$. Then, the backprojection coefficients may be computed as $c_1 = \phi^+ - \phi^- = (+1)(1) - (+1)(0) = 1$ (FIG. 16.). For $\hat{x} \in G_1 \cap G_3$, the $B_s$-curve will not enter $D_{41}$. Instead, it passes through a second T-curve twice, i.e., from $D_{43}$ to $D_{12}$ and from $D_7$ to $D_1$. From Table II, the jumps of n may only occur in the latter intersection. On the detector plane, this happens when $L(\theta)$ overlaps the line tangent to $\Gamma^{\pm 1}$. Then, the backprojection coefficients may be computed as $c_t = \phi^+ - \phi^- = (+1)(1) - (+1)(0) = 1$ (FIG. 15).

FIG. 13A and FIG. 13B summarize the filtering lines and the backprojection coefficients discussed above. In these figures, $L_0'$ is the line parallel to $L_0$ and $L_1$ denotes the L-line. To implement the proposed algorithm, the filtering lines cannot be truncated. Thus, the detector size should be large enough to cover the area bounded by $\Gamma_r$, $\Gamma_t$, $L_{max}$ and $L_{min}$, where $L_{max}$ and $L_{min}$ are the lines across the intersections of (1) $\Gamma_1$ and $\Gamma^{+2}$ and (2) $\Gamma$, and $\Gamma^{-2}$ respectively, and parallel to $L_0$ (FIG. 14). In certain embodiments, the required detector area can be determined by two factors: (1) the ratio of the pitch h and the scanning radius R and (2) the ratio of the object support radius r and the scanning radius R. If R is fixed, the required detector area grows as h or r increases.

Second Fast FBP Algorithm.

Again, the design of the second fast FBP algorithm starts with specifying new weights (Table III). By construction, n(s, x, $\alpha$) is continuous across all inter-PI lines. More importantly, a swap of two IPs takes place when a $B_s$-curve becomes tangent to a T-curve, and n(s, x, $\alpha$) changes from +1 to −1. The discontinuity of $\text{sgn}(\alpha \cdot \hat{y}(s))$ appears only when a $B_s$-curve is tangent to a T-curve from inside. Since both n(s, x, $\alpha$) and $\text{sgn}(\alpha \cdot \dot{y}(s))$ are discontinuous at that point, the function $\phi(s, x, \theta) := \text{sgn}(\alpha \cdot \dot{y}(s))n(s, x, \alpha)$ is continuous. Thus, the filtering operation along the tangent of the scanning trajectory is eliminated.

TABLE III

Weight Function for the Second Fast FBP Algorithm

| | $\widehat{S_1^*S_1^*}$ | $\widehat{S_2^*S_2^*}$ | $\widehat{S_3^*S_3^*}$ |
|---|---|---|---|
| $D_1$ | +1 | — | — |
| $D_2$ | — | +1 | — |
| $D_3$ | — | — | +1 |
| $D_5$ | +1, −1 | +1 | — |
| $D_6$ | +1, −1 | — | +1 |
| $D_7$ | +1 | +1, −1 | — |
| $D_8$ | — | +1, −1 | +1 |
| $D_9$ | +1 | — | +1, −1 |
| $D_{10}$ | — | +1 | +1, −1 |
| $D_{11}$ | −1, +1, −1 | +1 | +1 |
| $D_{12}$ | +1 | −1, +1, −1 | +1 |
| $D_{13}$ | +1 | +1 | −1, +1, −1 |
| $D_{41}$ | +1 | 0 | 0 |
| $D_{42}$ | 0 | +1 | 0 |
| $D_{43}$ | 0 | 0 | +1 |

A discontinuity of n can occur only when a $B_s$-curve intersects a T-curve or an L-curve. Follow the discussion in Section IV, jumps of n may occur when (1) a $B_s$-curve passes through a T-curve, i.e., from $D_{11}$ to $D_4$ or from $D_4$ to $D_{12}$ in FIGS. 11A and 11C, and (2) a $B_s$-curve passes through an L-curve, i.e., from $D_{42}$ to $D_{41}$ or from $D_{43}$ to $D_{41}$ in FIG. 8. On the detector plane, this gives two families of filtering lines: the lines tangent to $\Gamma^{\pm 2}$ or $\Gamma^{\pm 1}$ and the L-lines. Note that the filtering lines tangent to $\gamma^{\pm 1}$ are different from those for our first fast FBP algorithm (FIG. 15), because the discontinuity of n(s, x, $\alpha$) occurs on the different side of the cusp. Then, the backprojection coefficients can be calculated a $c_t = \phi^+ - \phi^- = (+1)(0) - (+1)(-1) = 1$ and $c_1 = \phi^+ - \phi^- = (+1)(1) - (+1)(0) = 1$.

The reconstruction formula for the second algorithm is the same as that for the first algorithm. The only difference lies in the selection of the filtering lines. For clarity, our second fast FBP algorithm is illustrated in FIGS. 16A-B. Because the filtering paths along the tangent of the scanning trajectory are eliminated, the required detector area is reduced by at least 30% (FIG. 14).

By Lemma 3 described below in the Examples section, there are two types of "line segments" according to different critical events. First, let us consider the "line segment" related to a critical event in Case 3. Recall that before entering $D_4$ the $B_s$-curve will be tangent to a T-curve. For the first algorithm, at the tangency the weight n changes from 1 to 0, then it does not change whether the Bs-curve enters $D_4$ across an A-curve or a T-curve. For the second algorithm, if the weight n changes from 1 to −1 at the tangency, then it will jump from −1 to 0 when the $B_s$-curve enters $D_4$. If the $B_s$-curve enters $D_4$ across an A-curve (i.e., the "line segment"; see FIG. 7), the FBP structure is ruined. Thus, the critical event in Case 3 will only affect the second algorithm, without damaging the FBP structure of the first algorithm. Then, let us consider the "line segment" related to a critical event in Case 5, which only occurs when r≧0.265 R. From the discussion in Section III.D such "a line segment" is the boundary of the one-IP and three-IP domains. Hence, for both the algorithms the weight n will jump from 1 to 0 if the $B_s$-curve enters $D_4$ across the "line segment", and the FBP structure is ruined. Consequently, the first algorithm is theoretically exact for r<0.265 R and not exact for 0.495 R≧r≧0.265 R, and the second algorithm is not exact for r≦0.495 R.

Since the algorithms are not always exact, it may be important to estimate what percentage of the Radon planes is incorrectly calculated. If the Radon planes with approximate weighting only have a small percentage, the algorithms can be considered quasi-exact, and we can still reconstruct with high image quality.

First, one must consider the incorrectly weighting planes caused by the critical event in Case 3. It appears in the area r<0.495 R. Let us fix x for r<0.495 R, denote the intersection of the Radon plane and the detector plane as L(θ), θ∈[0, 2π], run s over the three inter-PI arcs, and see what happens with x̂ and L(θ). Based on the discussion in Section III. E, for x̂ in $G_2$, if the critical event occurs, the $B_s$-curve will first intersect a T-curve, and then go cross an A-curve. For example, in FIG. 12 the $B_s$-curve will first intersect $T_1$, then enter $D_4$ across $A_3$. On the detector plane, this corresponds to that L(θ) intersects the tangent of $\Gamma^{+2}$ before the inter-PI line $\overline{\hat{s}_1^c \hat{s}_3^s}$ while L(θ) is rotated clockwise. Therefore, the Radon planes between the tangent of $\Gamma^{+2}$ and $\overline{\hat{s}_1^c \hat{s}_3^s}$ are not exactly weighted. Because the slope of $\overline{\hat{s}_1^c \hat{s}_3^s}$ is positive and the slope of the tangent of $\Gamma^{+2}$ is less than h/2πR, the percentage of the incorrectly weighted Radon planes is less than $$\rho = \frac{\beta}{\pi}, \text{ where } \alpha < \beta < 2\arctan\left(\frac{2}{\sqrt{3}}\tan\frac{\alpha}{2}\right), \alpha = \arctan\frac{h}{2\pi R}$$

(See Appendix). It is common that h/R<0.2 in practical applications, hence ρ<1.17%. For x̂ in $G_1$ ($G_3$), if the critical event occurs, the $B_s$-curve will first go across an A-curve, and then over a T-curve. On the detector plane, this corresponds to the case when L(θ) intersects the tangent to $\Gamma^{+1}$ ($\Gamma^{-1}$) before the inter-PI line $\overline{\hat{S}_3^e \hat{S}_2^s}$ while L(θ) is rotated clockwise. Hence, the Radon planes between the tangent of $\Gamma^{+1}$ ($\Gamma^{-1}$) and $\overline{\hat{S}_3^e \hat{S}_2^s}$ are not exactly weighted. Because the slope of $\overline{\hat{s}_3^e \hat{s}_2^s}$ is negative and the slope of the tangent of $\Gamma^{+1}$ ($\Gamma^{-1}$) is more than −0.35 h/R, the percentage of the incorrectly weighted Radon planes is less than ρ=2.57% for h/R=0.2.

Then, one must further consider the incorrectly weighting planes caused by the critical event in Case 5. Recall that the L-curves are used to split the domain $D_4$ into sub-domains, making the weight function n continuous across all the A-curves, and the cusps are the starting and ending points of the L-curves. If the endpoints of the L-curves are not the cusps, there will be small fractions (or "line segments") on the A-curves, making the weight function n discontinuous across them and ruining the FBP structure of our algorithms. It possibly occurs for r≧0.265 R. As discussed above, the Bs-curve will first enter a 1-IP domain from a 3-IP domain across the "line segment", and then pass through an L-curve. On the detector plane, this corresponds to that L(θ) intersects the inter-PI line $\overline{\hat{s}_3^e \hat{s}_2^s}$ before the L-line while L(θ) is rotated clockwise. Recall that if the cusp is not in $D_4$, $\hat{S}_2^s$ is possibly to the left of $\hat{S}_u$ or $\hat{S}_3^e$ is to the right of $\hat{S}_d$. Thus, the slope of $\overline{\hat{S}_3^e \hat{S}_2^s}$ is always more than −0.35 h/R.

Because the slope of the L-curve is never positive, the percentage of the incorrectly weighted Radon planes is less than ρ=2.57% for h/R=0.2. On the other hand, based on the discussion on Lemma 3, one or more cusps may possibly remain even when r≧0.265 R, which means that less "line segments" related to critical events will appear in Case 5, and in fact more Radon planes may be correctly weighted.

The implementation of these algorithms consists of one or more, and preferably all, of the following steps: Step 1) Differentiate each projection with respect to variable s; Step 2) For each $y_i(s)$, i={1, 2, 3}, perform the Hilbert transform of derivative data along the given filtering directions on the corresponding detector plane; Step 3) Backproject the filtered data on the inter-PI segments to reconstruct the object point. Differences between the algorithms described herein and some of the ones previously described include, but are not limited to, differences in triple-helices geometry the filtered data are backprojected on inter-PI segments and that there are two families of filtering lines for each algorithm so that each point on the detector plane will be filtered twice. Also, since the algorithms described herein allow shift-invariant filtration, all results are in Cartesian coordinates directly, and there is no coordinate transform necessary similar to what was used in the slow-FBP algorithm or BPF algorithm.

Previously published BPF algorithms for triple-source helical CBCT can indeed produce excellent image quality, FBP algorithms (either "slow" or "fast") are computationally desirable for several reasons, such as being amendable for parallel processing. In particular, while the computational structures of our BPF algorithm and FBP algorithms are quite similar, the FBP algorithms avoid densely sampled intermediate reconstruction in the PI-line-based coordinate system, and more importantly they can reconstruct a region of interest (ROI) or volume of interest (VOI) much more efficiently than the BPF counterpart. Note that ROI/VOI reconstruction is very common in medical imaging. A related technology called "interior tomography" is being actively developed to target this type of problems. Then, an interesting possibility would be to develop tripe-source interior CBCT.

The inventive two fast exact/quasi-exact FBP algorithms for triple-source helical CBCT have their advantages and disadvantages. From the perspective of exact reconstruction, the first algorithm is more desirable than the second algorithm because it is not affected by critical events in Case 3. However, in terms of efficient data acquisition, it may require a larger detector area than the second algorithm. In the medical CT field, the rectangular detector shape is most popular, and the helical pitch may be varied case by case. Therefore, it is practically possible to have projection data for reconstruction using either or both of the two fast FBP algorithms.

The methods disclosed herein can be practiced on any CT system. An example of a CT system and apparatus capable of implementing the methods is provided is an electron beam CT. In that framework, a curvilinear tungsten material or target can be arranged along a non-standard curve to be traced by an electro-magnetically driven electron-beam for formation of an X-ray source and collection of cone-beam data.

An exemplary electron beam CT comprises a vacuum chamber having an exterior surface, an underlying interior surface, and defines an enclosed space. At least a portion of the exterior surface can define or surround a subject cavity. The subject cavity is adapted to receive a subject. The subject cavity can be adapted to receive a human, a mouse or a rat, e.g.

The apparatus can further comprise a charged particle beam generator having a proximal and a spaced distal end. The electron beam generator can generate a flat or curved electron sheet. The electron beam generator can have a scanning speed from about 25 Hz to about 50 Hz. The apparatus can comprise a single electron beam generator or a plurality of electron beam generators.

The apparatus can include a focusing mechanism adapted to selectively focus charged particles generated by the charged particle beam generator and a target adapted to generate X-rays upon receipt of charged particles from the charged particle beam generator. If a plurality of electron beam generators are used, the apparatus may comprise a plurality of focusing mechanisms.

The apparatus further comprises a detector or a series of detectors surrounding the target. There are a large variety of detectors that can be used in the disclosed apparatuses, systems and methods. Two representative types are a) thin-film transistors (TFT, .alpha.-Si:H) and b) mono-crystalline silicone CCD/CMOS detectors. Although their quantum efficiency is high, the readout speed of TFT detectors is generally less than 30 frames per second, rarely reaching 100 frames per second. On the other hand, the readout speed of CCD/CMOS detectors can be extremely high, such as 10,000-30,000 frames per second, and are coupled with fiber-optical tapers, resulting in low quantum efficiency. For example, the 1000 Series camera from Spectral Instruments (Tucson, Ariz.), can be used. This camera is compact, measuring 92 by 92 by 168 mm. Two, three, and four-phase architecture CCDs from Fairchild Imaging (Milpitas, Calif.), E2V (Elmsford, N.Y.), Kodak (Rochester, N.Y.), and Atmel (San Jose, Calif.) can be placed in the selected camera. The readout and digitization can use 16-bit digitizer. The pixel readout rate can be varied from 50 kHz to 1 MHz. The gain of the analog processor can be modified under computer control to compensate for the gain change of the dual slope integrator at different readout speeds. The 1000 Series system offers fully programmable readout of sub arrays and independent serial and parallel register binning. In addition, specialized readout modes, such as time delay and integration (TDI) using an internal or external time base can be used. These capabilities allow the readout of only the area of the CCD of interest at variable resolution in order to optimize image signal to noise ratio.

To facilitate a better understanding of the present invention, the following examples of certain aspects of some embodiments are given. In no way should the following examples be read to limit, or define, the scope of the invention.

EXAMPLES

Example 1

To verify and showcase the fast FBP algorithms of the present invention, numerical tests were performed using the Clock phantom. This phantom consists of ellipses, as parameterized in Table IV. In the simulations, the origin of the reconstruction coordinate system was set to the center of each phantom. The spherical phantom support was of 375 mm for the experiment. Three sources were arranged uniformly along a circle with their corresponding detectors on the opposite side. The source-detector distance was 1000 mm. Projections were generated from 1000 view angles while the sources and the detectors were constantly moved along three helixes in one turn. The helix was of 750 mm in radius and 100 mm in pitch. The detector plane consisted of 1300×200 detection elements of 1.0×1.0 mm².

TABLE IV

Parameters of the Clock Phantom

| No. | $x_c$ | $y_c$ | $z_c$ | a | b | c | θ | ρ |
|---|---|---|---|---|---|---|---|---|
| 1 | 0 | 0 | 0 | 1 | 1 | 1 | 0 | 1 |
| 2 | 0 | 0.8 | 0 | 0.1 | 0.1 | 0.1 | 0 | 1 |
| 3 | 0.4 | 0.69 | 0.01 | 0.1 | 0.1 | 0.1 | 0 | 1 |
| 4 | 0.69 | 0.4 | 0.02 | 0.1 | 0.1 | 0.1 | 0 | 1 |
| 5 | 0.8 | 0 | 0.03 | 0.1 | 0.1 | 0.1 | 0 | 1 |
| 6 | 0.69 | −0.4 | 0.04 | 0.1 | 0.1 | 0.1 | 0 | 1 |
| 7 | 0.4 | −0.69 | 0.05 | 0.1 | 0.1 | 0.1 | 0 | 1 |
| 8 | 0 | −0.8 | 0.06 | 0.1 | 0.1 | 0.1 | 0 | 1 |
| 9 | −0.4 | −0.69 | 0.07 | 0.1 | 0.1 | 0.1 | 0 | 1 |
| 10 | −0.69 | −0.4 | 0.08 | 0.1 | 0.1 | 0.1 | 0 | 1 |
| 11 | −0.8 | 0 | 0.09 | 0.1 | 0.1 | 0.1 | 0 | 1 |
| 12 | −0.69 | 0.4 | 0.1 | 0.1 | 0.1 | 0.1 | 0 | 1 |
| 13 | −0.4 | 0.69 | 0.11 | 0.1 | 0.1 | 0.1 | 0 | 1 |
| 14 | 0 | 0.5 | 0 | 0.05 | 0.05 | 0.05 | 0 | 1 |
| 15 | 0.25 | 0.43 | −0.01 | 0.05 | 0.05 | 0.05 | 0 | 1 |
| 16 | 0.43 | 0.25 | −0.02 | 0.05 | 0.05 | 0.05 | 0 | 1 |
| 17 | 0.5 | 0 | −0.03 | 0.05 | 0.05 | 0.05 | 0 | 1 |
| 18 | 0.43 | −0.25 | −0.04 | 0.05 | 0.05 | 0.05 | 0 | 1 |
| 19 | 0.25 | −0.43 | −0.05 | 0.05 | 0.05 | 0.05 | 0 | 1 |
| 20 | 0 | −0.5 | −0.06 | 0.05 | 0.05 | 0.05 | 0 | 1 |
| 21 | −0.25 | −0.43 | −0.07 | 0.05 | 0.05 | 0.05 | 0 | 1 |
| 22 | −0.43 | −0.25 | −0.08 | 0.05 | 0.05 | 0.05 | 0 | 1 |
| 23 | −0.5 | 0 | −0.09 | 0.05 | 0.05 | 0.05 | 0 | 1 |
| 24 | −0.43 | 0.25 | −0.1 | 0.05 | 0.05 | 0.05 | 0 | 1 |
| 25 | −0.25 | 0.43 | −0.11 | 0.05 | 0.05 | 0.05 | 0 | 1 |

Figure 22:
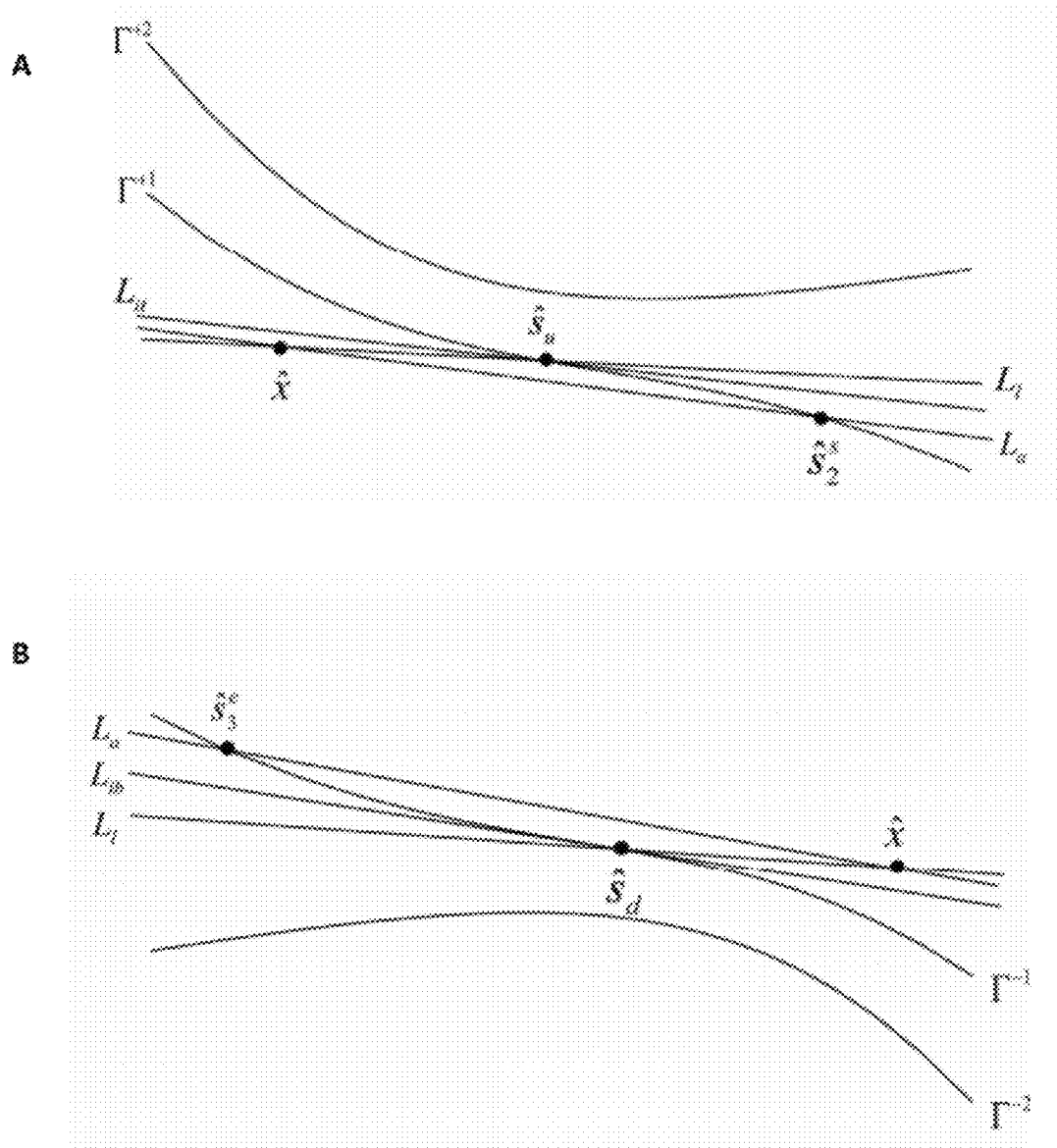
FIG. 22A is a graphical representations of the relationship among the inter-PI line $L_a$, L-line, $L_l$ and inflection line $L_{it}$ ($L_{ib}$) for $\hat{x}$ in $G_2$ and above $\hat{s}_u$.
FIG. 22B is a graphical representation of the relationship among the inter-PI line $L_a$, L-line, $L_l$ and inflection line $L_{it}$ ($L_{ib}$) for $\hat{x}$ in $G_2$ and above $\hat{s}_d$.
Figure 23:
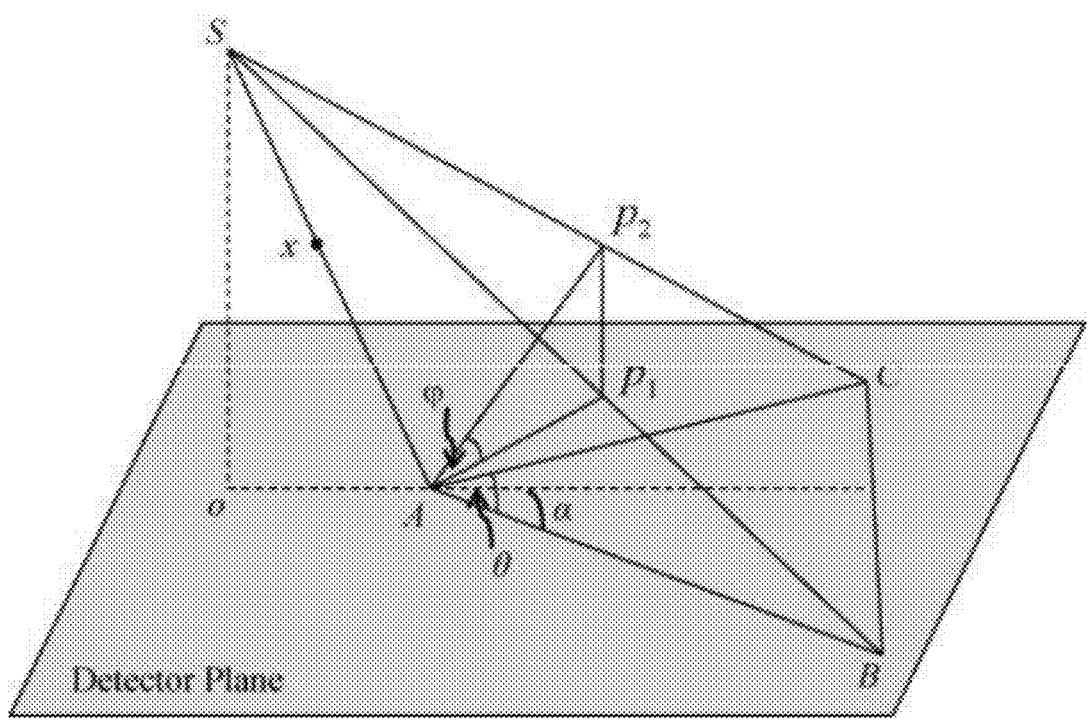
FIG. 23 is a schematic representation of the angular transformation from a spherical coordinate system to a detector.

The algorithms were coded in MATLAB and executed on a regular PC (Intel Core2 Duo CPU 3.06 GHz, 4 GB RAM). Reconstructed images are shown in FIG. 22. Our numerical results show that in the case of r=0.495 R both two algorithms produced high quality images.

Example 2

Auxiliary Lemmas were used as described below. A point was fixed at x∈Ω and its three associated inter-PI lines were found as shown in FIG. 3. Then, a source position was selected as s∈($s_j^3$, $s_j^e$), j∈{1, 2, 3} and how the inter-PI lines project onto the corresponding detector plane was determined. For simplicity, in this disclosure the projection of $y_i(s)$, j∈{1, 2, 3} on a detector plane is denoted by $\hat{S}_j$.

Lemma 1.

On a detector plane, the slopes of the projected inter-PI lines $\hat{S}_j^s \hat{S}_{j \bmod 3+1}^e$ and $\hat{S}_{(j+1)\bmod 3+1}^s \hat{S}_j^e$ are always positive, and that of the inter-PI line $\hat{S}_{j \bmod 3+1}^s \hat{S}_{(j+1)\bmod 3+1}^e$, j∈{1, 2, 3} is always negative.

Proof of Lemma 1.

Figure 18:
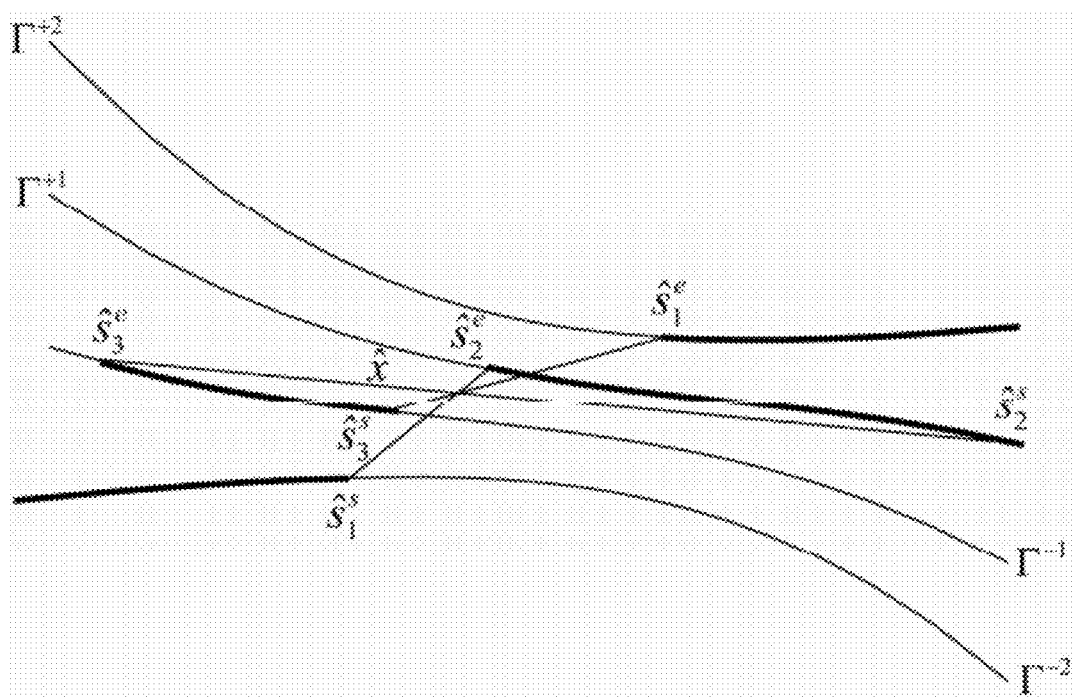
FIG. 18 is a graphical representation showing projected inter-PI lines on the detector plane, where the thick curve segments denote the inter-PI arcs.

Without loss of generality or wishing to be limited by theory, the source position was selected to be $y_1(s_0)$, $s_0 \in (s_1^s, s_1^e)$. By construction, $s_2^e - s_1^s < 2\pi$, $s_1^e - s_3^s < 2\pi$ and $s_3^e - s_2^s > 0$. Hence, the projections of $s_1^s$, $s_3^e$, and $s_3^s$ were always to the left of those of $s_2^e$, $s_2^s$, and $s_1^e$ respectively (FIG. 18). When $s \in (s_1^s, s_1^e)$ changed, the point $\hat{x}$, i.e., the projection of x onto the detector plane, was moved inside the region $G := G_1 \cup G_2 \cup G_3$. Clearly, $\hat{x}$ could reach its highest (respectively, lowest) position in the vertical direction when $\hat{x}$ was at the intersection of $\Gamma_1$ and $\Gamma^{+1}$ (respectively, of $\Gamma$, and $\Gamma^{-1}$). Also, the vertical coordinates at these points are $$v_{max} = 1.3794 \frac{Dh}{2\pi R} \text{ and } v_{min} = -1.3794 \frac{Dh}{2\pi R},$$

respectively. Moreover, the lowest point on $\Gamma^{+2}$ and the highest point on $\Gamma^{-2}$ are $$v'_{min} = 1.3801 \frac{Dh}{2\pi R} \text{ and } v'_{max} = -1.3801 \frac{Dh}{2\pi R}$$

respectively. Evidently, $v_{max} \leq v'_{min}$ and $v'_{max} \leq v_{min}$. Since $\hat{s}_1^s$ and $\hat{s}_3^s$ were to the left of $\hat{s}_2^e$ and $\hat{s}_1^e$, the slopes of the inter-PI lines $\overline{\hat{s}_1^s \hat{s}_2^e}$ and $\overline{\hat{s}_3^s \hat{s}_1^e}$ were positive for all $\hat{x}$ in G.

The inter-PI line $\overline{\hat{s}_2^s \hat{s}_3^e}$ was satisfied by EQUATION 18 below:

$$x_1 = Rt\cos s_2^s + R(1-t)\cos s_3^e \quad \text{(EQUATION 18)}$$
$$x_2 = Rt\sin s_2^s + R(1-t)\sin s_3^e$$
$$x_3 = \frac{h}{2\pi}t\left(s_2^s - \frac{2\pi}{3}\right) + \frac{h}{2\pi}(1-t)\left(s_3^e - \frac{4\pi}{3}\right),$$

where $t \in [0,1]$ and $s_2^s, s_3^e \in (s_0, s_0+2\pi)$.
By allowing $$x_1 = r_0 \cos \mu_0$$

$$x_2 = r_0 \sin \mu_0 \quad \text{(EQUATION 19)}$$

where $r_0 \in [0, 0.495\,R]$ and $\mu_0 \in [0, 2\pi]$.
The following was left:

$$\cos \frac{s_3^e - s_2^s}{2} = \frac{r_0 \sin(\mu_0 - s_2^s)}{\sqrt{R^2 + r_0^2 - 2Rr_0\cos(\mu_0 - s_2^s)}}, \text{ and} \quad \text{(EQUATION 20)}$$

then, EQUATION 20 was rewritten as EQUATION 21 below:

$$\cos \frac{s_3^e - s_2^s}{2} = \frac{\sin(\mu_0 - s_2^s)}{\sqrt{\left(\frac{R}{r_0} - \cos(\mu_0 - s_2^s)\right)^2 + \sin^2(\mu_0 - s_2^s)}}. \quad \text{(EQUATION 21)}$$

When $\mu_0 - s_2^e$ was fixed and $r_0$ was reduced, $$\left|\cos \frac{s_3^e - s_2^s}{2}\right|$$

decreased. Therefore, the right side of EQUATION 21 reached its maximum or minimum when $r_0$ is maximized, i.e. at $r_0 = 0.495\,R$. Those maximum and minimum values were numerically calculated (FIG. 19A), and shown below in EQUATIONS 22 and 23:

$$-0.4949 \leq \cos \frac{s_3^e - s_2^s}{2} \leq 0.4949 \quad \text{(EQUATION 22)}$$

or $2.1062 < s_3^e - s_2^s < 4.1770$ (EQUATION 23)

Next, it was shown that $0 \leq s_2^s - s_0 \leq 4.1773$ implied $$v_1(s_3^e - s_0) - v_2(s_2^s - s_0) > 0, \quad \text{(EQUATION 24)}$$

where $$v_1(s) = \frac{Dh}{2\pi R} \frac{s - 4\pi/3}{1 - \cos s} \text{ and } v_2(s) = \frac{Dh}{2\pi R} \frac{s - 2\pi/3}{1 - \cos s}.$$

Figure 19:
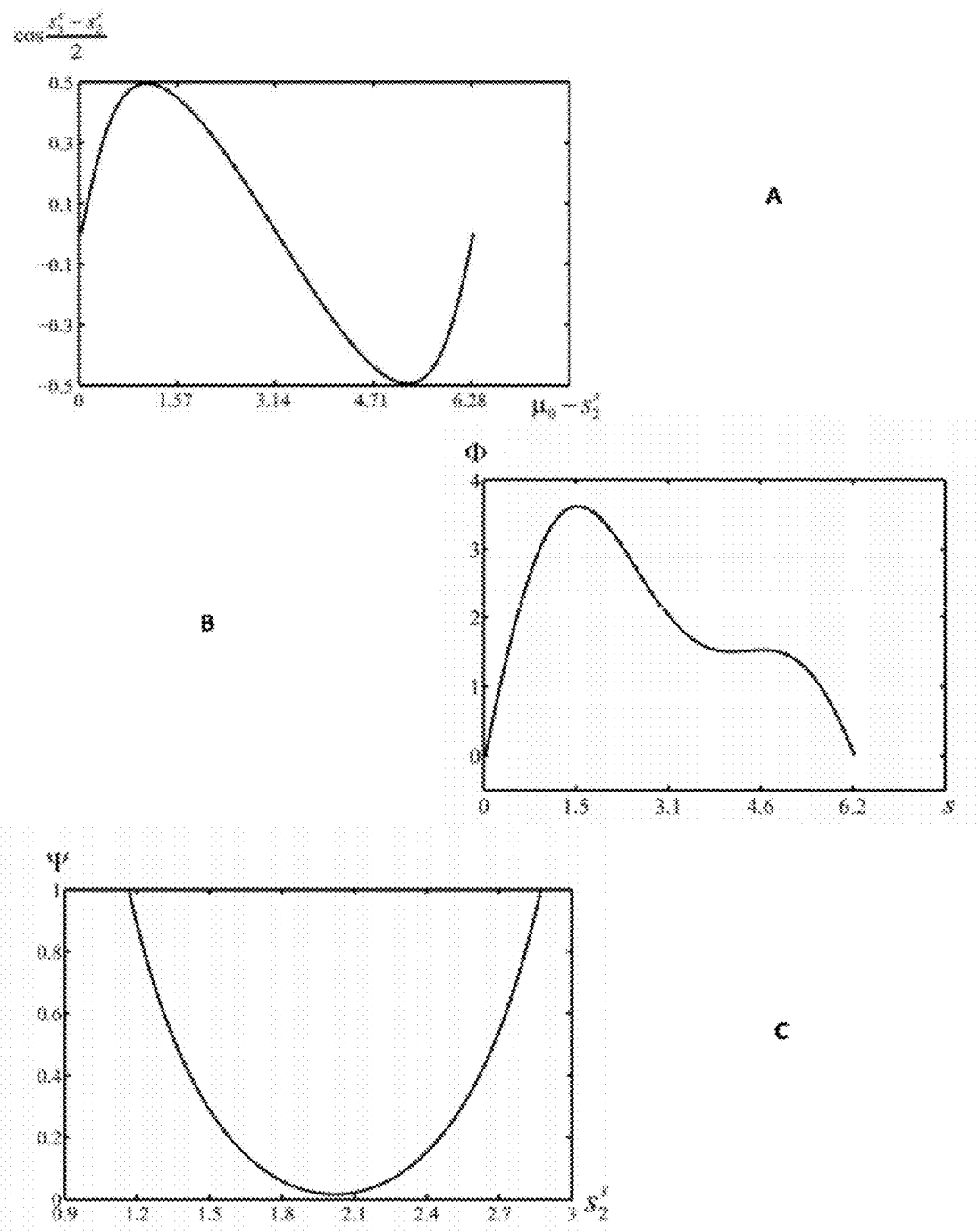
FIG. 19A is a graphical representation of a plot of EQUATION 20 with $r_0$=0.495 R.
FIG. 19B is a graphical representation of a plot of $\Phi_s$ over a range of s$\in$(0, 2$\pi$).
FIG. 19C is a graphical representation of a plot of $\psi(s_2^s)$ over a range of $0 \leq s_2^2 - s_0 \leq 4.1773$.

FIG. 19B shows the function $\Phi(s=1-\cos s - (s-4/3\pi)\sin s$ in the range $s \in (0, 2\pi)$, demonstrating that $\dot{v}_1(s)$ was always positive. Hence $v_1(s_3^e - s_0)$ was monotonically increasing. $s_3^e = s_2^s + 2.1062$ was fixed and the function) $\Psi(s_2^e) = v_1(s_3^e - s_0) - v_2(s_2^s - s_0)$ was plotted in FIG. 19C. Clearly, this function was always positive in the range $0 \leq s_2^s - s_0 \leq 4.1773$. Note that $s = 4.1773 + s_0$ was the intersection of $\Gamma_1$ and $\Gamma^{+1}$ and $\hat{s}_2^s$ could not be to the left of this point (otherwise, $\hat{x}$ is outside G). EQUATION 24 indicated that $\hat{s}_2^s$ was always lower than $\hat{s}_3^e$ in the vertical direction. Since $\hat{s}_2^s$ was to the right of $\hat{s}_3^s$, the slope of the inter-PI line $\overline{\hat{s}_2^s \hat{s}_3^e}$ was always negative. Due to symmetry, the other two cases $s \in (s_2^s, s_2^e)$ and $s \in (s_3^s, s_3^e)$ was handled similarly. This finishes the proof.

Lemma 2.

A T-curve cannot be tangent to an A-curve at an interior point of T.

Proof of Lemma 2.

The interior point of T-curve can be any point of the T-curve except an endpoint. It has been proved previously that a T-curve is smooth everywhere, except possibly at a cusp. When $s_i^e$, $i \in \{1, 2, 3\}$ is chosen to be the point where the cusp occurs. It was assumed that a T-curve was tangent to an A-curve at $\alpha(s)$. If $s = s_i^c \in (s_i^s, s_i^e)$, where $s_i^s, s_i^e$ were the endpoints of the T-curve, then the osculating plane $\Pi_e(x)$ intersected the helix $y_i(s)$ at only one point and it contained one inter-PI line. By construction, $\Pi_c(x)$ intersected the detector plane at the asymptote of the Tam-Danielson window boundary and $\hat{x}$ belonged to the asymptote. Connecting $\hat{x}$ and $\hat{s}_i^s$, $\hat{x}$ and $\hat{s}_i^e$ we detected two inter-PI lines. Clearly, $\Pi_e(x)$ could not contain any of them. By Lemma 1, the third inter-PI line had a negative slope, thus it would not overlap the asymptote. Hence, $\Pi_e(x)$ could not contain it. Consequently, $s \neq s_i^e$ and T-curve was smooth in a neighborhood of $\alpha(s)$. If $\theta$ was chosen to be the polar angle for the great circle $(x - y_i(s^e))^{\perp}$, $s^a \in \{s_i^s, s_i^e\}$, $i \in \{1, 2, 3\}$, then the A-curve could consist of all the unit vectors $\alpha_i(\theta) \in (x - y_i(s^e))^{\perp}$. Clearly, $\dot{\alpha}_1(\theta)$ could be perpendicular to $\alpha_1(\theta)$ and $(x - y_i(s^a))$. By construction, the T-curve was tangent to the A-curve at $\alpha(s)$. Hence, $\dot{\alpha}(s)$ was be parallel to $\dot{\alpha}_1(\theta)$. That is, $\dot{\alpha}(s)$ was perpendicular to $\alpha_1(\theta)$ and $(x - y_i(s^a))$. Because $\dot{\alpha}(s)$ was also perpendicular to $(x - y_i(s^1))$, $s^1 \in (s_i^s, s_i^e)$, $(x - y_i(s^1))$ was parallel to $(x - y_i(s^a))$ and $s^1 = s^a$, which contradicted the assumption that $s^i$ is an inner point of the T-curve. This finishes the proof.

Lemma 3.

Case 1, 2, 4, 6, 7 do not occur for $r < 0.495\,R$ and Case 5 does not occur for $r < 0.265\,R$.

Proof of Lemma 3.

Figure 20:
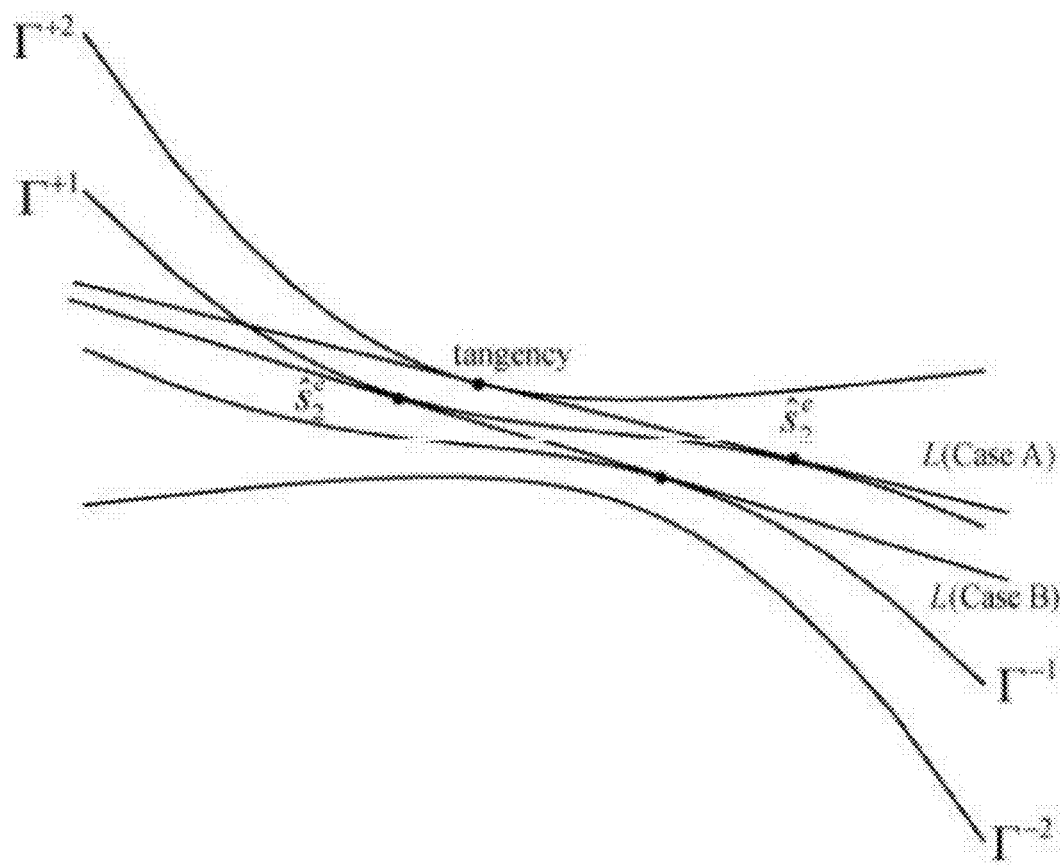
FIG. 20 is a graphical representation for possible locations of the "critical event" for Case 4.
Figure 21:
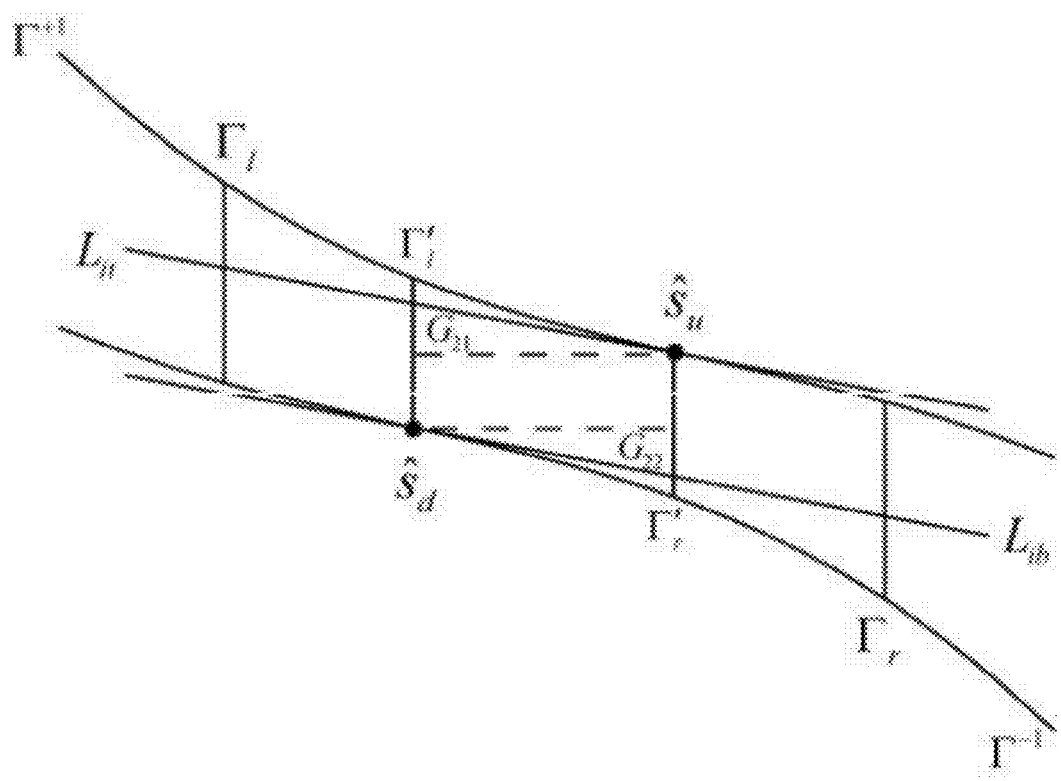
FIG. 21 is a graphical representation illustrating regions $G_{21}$ and $G_{22}$.

Cases 1 and 2 were impossible because they mean that there can be a plane containing three inter-PI lines or tangent to three inter-PI arcs. In Case 4, there can be one plane $\Pi$ containing one inter-PI line and tangent to two inter-PI arcs. If one assumes this inter-PI line is $\overline{s_1^s s_2^e}$, chooses a point $s = s_1^s$ on $y_i(s)$ and denotes $L = \Pi \cap DP(s_0)$, then by construction, on the detector plane $\hat{x}$ is on $\Gamma^{+1}$ and it overlaps $\hat{s}_2^e$. Then, L may tangent to $\Gamma^{+1}$ and $\Gamma^{+4}$ or $\Gamma^{-1}$, see FIG. 20. Because the points of tangency are on the inter-PI arcs, the endpoint $\hat{s}_1^e$ is to the left of the tangency for case A and $\hat{s}_3^e$ was to the right of the tangency for case B. Connecting $\hat{s}_1^e$ and $\hat{x}$ (or $\hat{s}_3^s$ and $\hat{x}$) we find that the slope of the inter-PI line $\overline{\hat{s}_3^s \hat{s}_1^e}$ could be negative. By Lemma 1, these two cases were impossible.

In Case 5, there was one plane containing one inter-PI line and tangent to one inter-PI arc at the inflection point. Thus, the inter-PI line on the detector overlapped the inflection line, i.e., $\widehat{\hat{s}_2^s \hat{s}_3^e}$ overlapped $L_{it}$, when $s_2^s = s_u$ and $s_3^e = 2s_u$, where $s_u$ is difference between $s_2^1$ and $s_3^e$. When looking at EQUATION 21 and $\mu_0 - s_2^e$ is fixed, the absolute value of $$\cos \frac{s_3^e - s_2^s}{2}$$

was monotonically decreasing when $r_0$ was reduced. Then, the range of $s_3^e - s_2^e$ was narrowed. In other words, the difference between $s_e^e$ and $s_2^e$ became closer to $\pi$. Case 5 occurred when $s_3^e - s_2^e = s_u$. If order to exclude Case 5, the range of $s_3^e - s_2^e$ could not cover the value $s_u = 2.6053$. Hence, the minimum range of $s_3^e - s_2^e$ is $2.6053 < s_3^e - s_2^e 2\pi - 2.6053$. That is, $$-0.2649 < \cos \frac{s_3^e - s_2^s}{2} < 0.2649 \text{ and } \cos \frac{s_3^e - s_2^s}{2}$$

reached its extreme when $r_0 = 0.265$ R. From EQUATIONS 21 and 22 we have $s_3^e - s_2^s = s_u$ only for $r \geq 0.265$ R thereby contradicting our condition. Hence, Case 5 was impossible for $r < 0.265$ R.

In Case 6, a T-curve will intersect one A-curve twice before meeting a cusp. Suppose this took place at inter-PI arc $\widehat{S_1^s S_1^e}$. A point $s = s_1^s$ on $y_1(s)$ was chosen and observations of what happens on the detector plane when s moves were taken. By construction, the plane $\Pi$ containing $\dot{y}_1(s)$ and x intersected the detector plane at the line L which was parallel to the helix tangent across $\hat{x}$. At $s = s_1^s$, $\hat{x}$ was on $\Gamma^{+1}$ and $\Pi$ contained inter-PI line $\widehat{\hat{s}_1^s \hat{s}_2^e}$. As s moved along $y_1(s)$, $\hat{x}$ moved downwards. Notice that L was parallel to the asymptote of the Tam-Dannielson window, so it would not intersect $\Gamma^{-2}$ provided that $\hat{x}$ moved across the asymptote, at where the cusp occurred. Hence, $\Pi$ would not contain the inter-PI line $\widehat{\hat{s}_1^s \hat{s}_2^e}$ and Case 6 was impossible. By Lemma 2, Case 7 was impossible. This finishes the proof.

Lemma 4.

The inflection point $\hat{s}_u(\hat{s}_d)$ is inside the inter-PI arc when $\hat{x}$ is in $G_{21}$ ($G_{22}$).

Proof of Lemma 4.

By Lemma 3, any point in the area $r < 0.265$ R had three cusps in the diagram. Note that there was one IP in each inter-PI arc within $D_4$. Since all three cusps were in $D_4$, an osculating plane of one inter-PI arc intersected two other inter-PI arcs exactly once at one point. Assuming that this osculating plane $\Pi_e$ contained x and considering $\Pi_e$ of the second inter-PI arc (i.e., of $y_2(s)$). $s_1^0$ was set to be the point where it intersected the first inter-PI arc (i.e., on $y_1(s)$). s was moved along the first inter-PI arc and the results were observed with $\hat{x}$ on the detector when $s = s_1^s$, $\hat{x}$ entered the Zhao window through $\Gamma^{+1}$, and when $s = s_{12}^0$, $\hat{x}$ belongs to $L_u$. As follows from the diagram, the point $s_u$ must be inside the second inter-PI arc, i.e., between $\hat{s}_2^s$ and $s_2^e$. As the point s moved further, the difference $s_2^s - s$ became smaller, and the point $\hat{s}_2^e$ moved to the right of $\hat{s}_u$ along $\Gamma^+$. The inter-PI line $\widehat{\hat{s}_1^s \hat{s}_2^e}$ had a positive slope. Thus, as long as $\hat{x}$ was inside $G_{21}$, the point $\hat{s}_2^e$ was always to the left of $\hat{s}_u$. The case where $\hat{x}$ was in $G_{22}$ can be similarly treated. This proves Lemma 4.

Lemma 5.

An L-curve never intersects an A-curve, for $r < 0.265$ R.

Proof of Lemma 5.

If an L- and A-curve intersect, an L-line through $\hat{x}$ can overlap the inter-PI line. One point on the inter-PI arc $\widehat{S_3^s S_3^e}$ was chosen and the slope of the inter-PI line was considered on the corresponding detector plane. By construction, an L-curve always started from a cusp of a T-curve and ended on a cusp of another T-curve. For the osculating plane $\Pi_e$, its intersection with the detector plane was the line tangent to $\Gamma^{+1}$ ($\Gamma^{-1}$) at $\hat{s}_u(\hat{s}_d)$. By Lemma 4, the endpoints of the inter-PI arc on $\Gamma^{+1}$ ($\Gamma^{-1}$) were on different sides of $\hat{s}_u(\hat{s}_d)$, and one of them on the right (left) side was also an endpoint of the inter-PI line for helices $y_2(s)$ and $y_3(s)$, and was denoted as $\hat{s}_2^s(\hat{s}_3^e)$ in FIG. 22.

If $\hat{x}$ was in $G_2$ and above $\hat{s}_u$, the L-line was formed by connecting $\hat{x}$, $\hat{s}_u$, and the inter-PI line was formed connecting $\hat{x}$, $\hat{s}_2^s$. If z was in $G_2$ and below $\hat{s}_d$, we formed the L-line by connecting $\hat{x}$, $\hat{s}_d$, and the inter-PI line was formed by connecting $\hat{x}$, $\hat{s}_3^e$. Clearly, in any case the slope of L-line was between zero and the slope of the inter-PI line. That is, the L-line could not overlap the inter-PI line. For other $\hat{x}$, the L-line was parallel to the u axis. By Lemma 1, it was always between two inter-PI lines and could not overlap with any of them. For the point on other inter-PI arcs, the situation was the same. This finishes the proof.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

Throughout this application, various publications are referenced. The disclosures of these publications in their entireties are hereby incorporated by reference into this application in order to more fully describe the features of the invention and/or the state of the art to which this pertains. The references disclosed are also individually and specifically incorporated by reference herein for the material contained in them that is discussed in the portion of this disclosure in which the reference is relied upon.

G. Wang, C. R. Crawford, and W. A. Kalender, "Guest editorial-Multirow detector and cone-beam, spiral/helical CT," *Medical Imaging, IEEE Transactions on*, vol. 19, pp. 817-821, 2000.

T. G. Flohr, C. H. McCollough, H. Bruder, M. Petersilka, K. Gruber, C. Süβ, M. Grasruck, K. Stierstorfer, B. Krauss, and R. Raupach, "First performance evaluation of a dual-source CT (DSCT) system," *European Radiology*, vol. 16, pp. 256-268, 2006.

M. Vannier and G. Wang, "Spiral CT refines imaging of temporal bone disorders," *Diagnostic imaging*, vol. 15, p. 116-121, 1993.

G. Wang, S. Zhao, H. Yu, C. Miller, P. Abbas, B. Gantz, S. Lee, and J. Rubinstein, "Design, analysis and simulation for development of the first clinical micro-CT scanner1," *Academic Radiology*, vol. 12, pp. 511-525, 2005.

G. Wang, T.-H. Lin, P.-C. Cheng, and D. M. Shinozaki, "A general cone-beam reconstruction algorithm," *IEEE Transactions on Medical Imaging*, vol. 12, p. 486, 1993.

A. Katsevich, "Theoretically exact filtered backprojection-type inversion algorithm for spiral CT," *SIAM Journal on Applied Mathematics*, vol. 62, p. 2012, 2002.

S. S. Orlov, "Theory of three-dimensional reconstruction. 1. Conditions of a complete set of projections," *Sov. Phys. Crystallogr*, vol. 20, pp. 312-314, 1975.

I. Gel'fand and M. Graev, "Crofton's function and inversion formulas in real integral geometry," *Functional Analysis and Its Applications*, vol. 25, pp. 1-5, 1991.

H. Rullgård, "An explicit inversion formula for the exponential Radon transform using data from 180," Arkiv för Matematik, vol. 42, pp. 353-362, 2004.

G. Wang, Y. Ye, and H. Yu, "Approximate and exact cone-beam reconstruction with standard and non-standard spiral scanning," *Physics in Medicine and Biology*, vol. 52, pp. 1-13, 2007.

J. Zhao, M. Jiang, T. Zhuang, and G. Wang, "An exact reconstruction algorithm for triple-source helical cone-beam CT," *Journal of X-Ray Science and Technology*, vol. 14, p. 191, 2006.

J. Zhao, Y. Jin, Y. Lu and G. Wang, "A Filtered Backprojection Algorithm for Triple-Source Helical Cone-Beam CT," *Medical Imaging, IEEE Transactions on*, vol. 28, pp. 384-393, 2009.

The invention claimed is:

1. A computed tomography (CT) imaging method comprising:

scanning an object using triple-source helical cone-beam computed tomography (CBCT) to acquire projection data relating to the object being imaged, where each x-ray source of the CBCT is disposed opposite a detector and has a scanning radius that is a distance R from a rotation axis, and where each detector covers a field of view less than 0.495 R; and reconstructing the scanned portion of the object into an image by performing a computationally efficient filtered backprojection (FBP) and theoretically exact/quasi-exact algorithm to generate image data.

2. The method of claim 1, further comprising:

supporting the object in a stationary position; and moving each source of the triple-source and its associated detector about the object at a constant speed to generate three spiral scans with source trajectories $y_1(s)$, $y_2(s)$, and $y_3(s)$ defined as:

$$\begin{cases} y_1(s) = \left(R\cos s,\ R\sin s,\ \frac{h}{2\pi}s\right) \\ y_2(s) = \left(R\cos\left(s+\frac{2}{3}\pi\right),\ R\sin\left(s+\frac{2}{3}\pi\right),\ \frac{h}{2\pi}s\right) \\ y_3(s) = \left(R\cos\left(s+\frac{4}{3}\pi\right),\ R\sin\left(s+\frac{4}{3}\pi\right),\ \frac{h}{2\pi}s\right) \end{cases}$$

where R is the distance from the x-ray source to the rotation axis, h is helical pitch, s is a scan path corresponding to source position.

3. A method of computing images derived from triple-source spiral computed tomography scan with three detectors, comprising the steps of:

(a) collecting cone beam data from three detectors during a scan of an object;

(b) for each source position $y_j(s)$, $j\in\{1, 2, 3\}$, identifying two families of lines on a detector plane DP(s) corresponding to a source position s and containing the corresponding detector and intersecting the cone beam, and two families of lines include:

i. a first family of lines parallel to $L_0$, where
$L_0$ is the projection of the helical tangent at current source position;

ii. a second family of lines tangent to $\Gamma^{+1}$ and $\Gamma^{-1}$, or parallel to the horizontal axis of the plane DP(s), where $\Gamma^{+1}$ is the projection of the helical turn $y_{j\mathrm{mod}3+1}(s)$ defined by $s<q\leq s+2\pi$ onto the plane DP(s);

$\Gamma^{-1}$ is the projection of the helical turn $y_{(j+1)\mathrm{mod}3+1}(s)$ defined by $s<q\leq s+2\pi$ onto the plane DP(s);

q is the parameter along the scan path which describes the point being projected;

(c) computing a derivative of the cone beam data with respect to the source position;

(d) performing Hilbert transform of the derivative of the cone beam data along the two families of lines, where the Hilbert transform is a convolution between the derivative of the cone beam data and a kernel function $h(t)=1/(\pi t)$;

(e) back projecting said filtered data to form a precursor of said image; and (f) repeating steps a, b, c, d and e to obtain an image.

4. The method of claim 3, wherein identifying the second family of lines includes:

the lines tangent to $\Gamma^{+1}$, when the projection of point x onto DP(s) is located in the area bounded by $\Gamma_l$, $L_{it}$, and $\Gamma^{+1}$;

the lines tangent to $\Gamma^{-1}$, when the projection of point x onto DP(s) is located in the area bounded by $\Gamma_r$, $L_{ib}$, and $\Gamma^{-1}$;

the lines parallel to the horizontal axis of the plane DP(s), when the projection of x onto DP(s) is located in the area bounded by $\Gamma_l$, $\Gamma_r$, $L_{it}$, $L_{ib}$, $\Gamma^{+1}$ and $\Gamma^{-1}$, where $\Gamma_l$ and $\Gamma_r$ are the projections of the object support limitation r=0.495 R onto DP(s);

$L_{it}$ is the inflection line of $\Gamma^{+1}$;

$L_{ib}$ is the inflection line of $\Gamma^{-1}$;

r is the radius of the object support, and

R is the radius of the scanning trajectory.

5. The method of claim 3, wherein the back projection step(e) includes:
  (ei) fixing a reconstruction point x, which represents a point inside the object being scanned where it is required to reconstruct the image;
  (eii) determining the three inter-PI arcs for x;
  (eiii) finding the projection $\hat{x}$ of x onto a detector plane DP(s);
  (eiv) identifying lines from the two families of lines and points on the said lines that are passing through the said projection $\hat{x}$;
  (ev) computing contribution from filtered cone beam data to the image being reconstructed at the point x by multiplying $$-\frac{1}{4\pi^2|x - y(s)|};$$

(evi) adding the contribution from filtered cone beam data to the image being reconstructed at the point x according to the three inter-PI arcs;
  (evii) going to step (ei) and choose a different reconstruction point x.

6. The method of claim 5, wherein the three inter-PI arcs for x are determined according to the following rules:

the endpoints of the inter-PI arc on a first helical turn $y_1(s)$ are $s=s_1^s$ and $s=s_1^e$, $s_1^e > s_1^s$;

the endpoints of the inter-PI arc on a second helical turn $y_2(s)$ are $s=s_2^s$ and $s=s_2^e$, $s_2^e > s_2^s$;

the endpoints of the inter-PI arc on a third helical turn $y_3(s)$ are $s=s_3^s$ and $s=s_3^e$, $s_3^e > s_3^s$;

$|s_2^e - s_1^s| < 2\pi$;

$|s_3^e - s_2^s| < 2\pi$;

$|s_1^e - s_3^s| < 2\pi$;

the line connecting $y_1(s_1^e)$ and $y_3(s_3^s)$ passes through x;
the line connecting $y_2(s_2^e)$ and $y_1(s_1^s)$ passes through x;
the line connecting $y_3(s_3^e)$ and $y_2(s_2^e)$ passes through x.

7. A method of computing images derived from triple-source spiral computed tomography scan with three detectors, comprising the steps of:
  (a) collecting cone beam data from three detectors during a scan of an object;
  (b) for each source position $y_j(s)$, $j \in \{1, 2, 3\}$, identifying two families of lines on a detector plane DP(s) corresponding to a source position s and containing the corresponding detector and intersecting the cone beam, and two families of lines include:
    i. a first family of lines tangent to $\Gamma^{+2}$ and $\Gamma^{-2}$, where
      $\Gamma^{+2}$ is the projection of the current helical turn defined by $s < q < s+2\pi$ onto the plane DP(s);
      $\Gamma^{-2}$ is the projection of the current helical turn defined by $s-2\pi < q < s$ onto the plane DP(s);
    ii. a second family of lines tangent to $\Gamma^{+1}$ and $\Gamma^{-1}$, or parallel to the horizontal axis of the plane DP(s), where
      $\Gamma^{+1}$ is the projection of the helical turn $y_{j \mod 3+1}(s)$ defined by $s < q < s+2\pi$ onto the plane DP(s);
      $\Gamma^{-1}$ is the projection of the helical turn $y_{(j+1) \mod 3+1}(s)$ defined by $s < q < s+2\pi$ onto the plane DP(s);
  (c) computing the derivative of the cone beam data with respect to the source position;
  (d) performing the Hilbert transform of the derivative of the cone beam data along the two families of lines, where the Hilbert transform is a convolution between the derivative of the cone beam data and a kernel function $h(t)=1/(\pi t)$;
  (e) back projecting said filtered data to form a precursor of said image; and
  (f) repeating steps a, b, c, d and e until an image of the object is completed.

8. The method of claim 7, wherein identifying the first family of lines includes:
  the lines tangent to $\Gamma^{+2}$, when the projection of x onto DP(s) is located above $L_0$;
  the lines tangent to $\Gamma^{-2}$, when the projection of x onto DP(s) is located below $L_0$;
  where $L_0$ is the projection of the helical tangent at current source position.

9. The method of claim 7, wherein identifying the second family of lines includes:
  the lines tangent to $\Gamma^{+1}$, when the projection of x onto DP(s) is located in the area bounded by $\Gamma_l$, $L_{it}$ and $\Gamma^{+1}$;
  the lines tangent to $\Gamma^{-1}$, when the projection of x onto DP(s) is located in the area bounded by $\Gamma_r$, $L_{ib}$ and $\Gamma^{-1}$;
  the lines parallel to the horizontal axis of the plane DP(s), when the projection of x onto DP(s) is located in the area bounded by $\Gamma_l$, $\Gamma_r$, $L_{it}$, $L_{ib}$, $\Gamma^{+1}$ and $\Gamma^{-1}$, where $\Gamma_l$ and $\Gamma_r$ are the projections of the object support limitation r=0.495 R onto DP(s);

$L_{it}$ is the inflection line of $\Gamma^{+1}$;

$L_{ib}$ is the inflection line of $\Gamma^{-1}$;

r is the radius of the object support, and

R is the radius of the scanning trajectory.

10. The method of claim 7, wherein the back projection step(e) includes:
  (ei) fixing a reconstruction point x, which represents a point inside the object being scanned where it is required to reconstruct the image;
  (eii) determining the three inter-PI arcs for x;
  (eiii) finding the projection $\hat{x}$ of x onto a detector plane DP(s);
  (eiv) identifying lines from the two families of lines and points on the said lines that are passing through the said projection $\hat{x}$;
  (ev) computing contribution from filtered cone beam data to the image being reconstructed at the point x by multiplying $$-\frac{1}{4\pi^2|x - y(s)|};$$

(evi) adding the contribution from filtered cone beam data to the image being reconstructed at the point v according to the three inter-PI arcs;
  (evii) going to step (ei) and choose a different reconstruction point x.

11. The method of claim 7, wherein the three inter-PI arcs for x are determined according to the following rules:

the endpoints of the inter-PI arc on a first helical turn $y_1(s)$ are $s=s_1^s$ and $s=s_1^e$, $s_1^e > s_1^s$;

the endpoints of the inter-PI arc on a second helical turn $y_2(s)$ are $s=s_2^s$ and $s=s_2^e$, $s_2^e > s_2^s$;

the endpoints of the inter-PI arc on a third helical turn $y_3(s)$ are $s=s_3^s$ and $s=s_3^e$, $s_3^e > s_3^s$;

$|s_2^e - s_1^s| < 2\pi$;

$|s_3^e - s_2^s| < 2\pi$;

$|s_1^e - s_3^s| < 2\pi$;

the line connecting $y_1(s_1^e)$ and $y_3(s_3^s)$ passes through x;
the line connecting $y_2(s_2^e)$ and $y_1(s_1^s)$ passes through x;
the line connecting $y_3(s_3^e)$ and $y_2(s_2^e)$ passes through x.

* * * * *